United States Patent
Li et al.

(10) Patent No.: US 9,968,664 B2
(45) Date of Patent: *May 15, 2018

(54) FUSION MOLECULE BASED ON NOVEL TAA VARIANT

(71) Applicant: The Regents of the University of California, Oakland, CA (US)

(72) Inventors: Zhenhua Li, Los Angeles, CA (US); Arie S. Belldegrun, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/293,710

(22) Filed: Oct. 14, 2016

(65) Prior Publication Data

US 2017/0119866 A1    May 4, 2017

Related U.S. Application Data

(60) Continuation of application No. 15/073,162, filed on Mar. 17, 2016, now Pat. No. 9,492,520, which is a division of application No. 13/740,099, filed on Jan. 11, 2013, now Pat. No. 9,322,010, which is a continuation of application No. 12/520,084, filed as application No. PCT/US2007/088676 on Dec. 21, 2007, now Pat. No. 8,378,084.

(60) Provisional application No. 60/876,863, filed on Dec. 22, 2006.

(51) Int. Cl.
| | |
|---|---|
| A61K 39/00 | (2006.01) |
| A61K 45/06 | (2006.01) |
| C07K 14/53 | (2006.01) |
| C12N 9/88 | (2006.01) |
| C12N 5/078 | (2010.01) |
| C07K 14/535 | (2006.01) |
| G01N 33/574 | (2006.01) |
| C12N 9/96 | (2006.01) |
| A61K 38/19 | (2006.01) |

(52) U.S. Cl.
CPC ........ *A61K 39/0011* (2013.01); *A61K 38/193* (2013.01); *A61K 45/06* (2013.01); *C07K 14/535* (2013.01); *C12N 5/0634* (2013.01); *C12N 9/88* (2013.01); *C12N 9/96* (2013.01); *C12Y 402/01001* (2013.01); *G01N 33/57411* (2013.01); *G01N 33/57438* (2013.01); *A61K 2039/5154* (2013.01); *A61K 2039/5156* (2013.01); *A61K 2039/5158* (2013.01); *A61K 2039/55522* (2013.01); *C07K 2319/75* (2013.01); *C12N 2501/22* (2013.01); *C12N 2501/2302* (2013.01); *C12N 2501/24* (2013.01); *C12N 2501/70* (2013.01); *G01N 2333/988* (2013.01)

(58) Field of Classification Search
CPC .... A61K 2039/5154; A61K 2039/5156; A61K 2039/5158; A61K 2039/55522; A61K 38/193; A61K 39/0011; A61K 45/06; C07K 14/535; C07K 2319/75; C12N 5/0634
USPC ............ 424/93.21, 93.71, 277.1, 192.1
See application file for complete search history.

(56) References Cited

U.S. PATENT DOCUMENTS

| | | |
|---|---|---|
| 8,378,084 B2 | 2/2013 | Li et al. |
| 8,741,306 B2 | 6/2014 | Belldegrun et al. |
| 9,322,010 B2 | 4/2016 | Li et al. |
| 9,492,520 B2 | 11/2016 | Li et al. |
| 2015/0010587 A1 | 1/2015 | Belldegrun et al. |

FOREIGN PATENT DOCUMENTS

| | | |
|---|---|---|
| WO | 9534650 | 12/1995 |
| WO | 01060317 | 8/2001 |
| WO | 2005037083 | 4/2005 |

OTHER PUBLICATIONS

Hernandez et al. (2003) Clin. Canc. Res., vol. 9, 1906-1916.*
Atkins et al., Carbonic Anhydrase IX Expression Predicts Outcome of Interleukin 2 Therapy for Renal Cancer, Clinical Cancer Research, vol. 11, No. 10, May 2005, pp. 3714-3721.
Bui et al., Prognostic Value of Carbonic Anhydrase Ix And KI67 As Predictors of Survival for Renal Clear Cell Carcinoma, Journal of Urology, Baltimore, MD, US, vol. 171, No. 6, Jun. 1, 2004, pp. 2461-2466.
Hernandez et al., Novel Kidney cancer Immunotherapy Based on the Granulocyte Macrophage Colony-stimulating Factor and Carbonic Anhydrase IX Fusion Gene, Clin. Cancer Res., vol. 9, May 2003, pp. 1906-1916.
Li et al., The Use of MN/CA9 Gene Expression in Identifying Malignant Solid Renal Tumors, European Urology, Elsevier BV, NL, vol. 49, No. 2, Feb. 1, 2006, pp. 401-405.
Mukouyama et al., Generation of kidney cancer-specific antitumor immune responses using peripheral blood monocytes transduced with a recombinant adenovirus encoding carbonic anhydrase 9, Clinical Cancer Research, vol. 10, No. 4, Feb. 15, 2004, pp. 1421-1429.
Opavsky et al., Human MN/CA9 Gene, a Novel Member of the Carbonic Anhydrase Family: Structure and Exon to Protein Domain Relationships, Genomics, vol. 33, No. 3, 1996, pp. 480-487.
Shimizu et al., Induction of antigen specific cellular immunity by vaccination with peptides from MN/CA IX in renal cell carcinoma, Oncology Reports, vol. 10, No. 5, Sep. 2003, pp. 1307-1311.
Graddis et al., Dendritic cell immunotherapy using CA9-GM-CSF fusion protein, Journal of Immunology, Annual Meeting of the American-Association-of-Immunologists, vol. 176, No. Suppl. S, Apr. 2006, p. S259.

(Continued)

*Primary Examiner* — Anne Marie S Wehbe
(74) *Attorney, Agent, or Firm* — Kilpatrick Townsend & Stockton LLP

(57) ABSTRACT

This invention provides novel carbonic anhydrase (CAIX) nucleic acid and peptide sequences, as well as related methods and compositions, including anti-cancer immunogenic agent(s) (e.g. vaccines and chimeric molecules) that elicit an immune response specifically directed against cancer cells expressing a CAIX antigenic marker. The novel CAIX variant and related compositions are useful in a wide variety of treatment modalities including, but not limited to protein vaccination, DNA vaccination, and adoptive immunotherapy.

16 Claims, 1 Drawing Sheet

(56) References Cited

OTHER PUBLICATIONS

Tso et al., Induction of G250-targeted and T-cell-mediated antitumor activity against renal cell carcinoma using a chimeric fusion protein consisting of G250 and granulocyte/monocyte-colony stimulating factor, Cancer Research, American Association for Cancer Research, vol. 61, No. 21, Nov. 1, 2001, pp. 7925-7933.

Vissers et al., The Renal Cell Carcinoma-associated Antigen G250 Encodes a Human Leukocyte Antigen (HLA)-A2.1-restricted Epitope Recognized by Cytotoxic T Lymphocyte, Cancer Research, vol. 59, Nov. 1999, pp. 5554-5559.

* cited by examiner

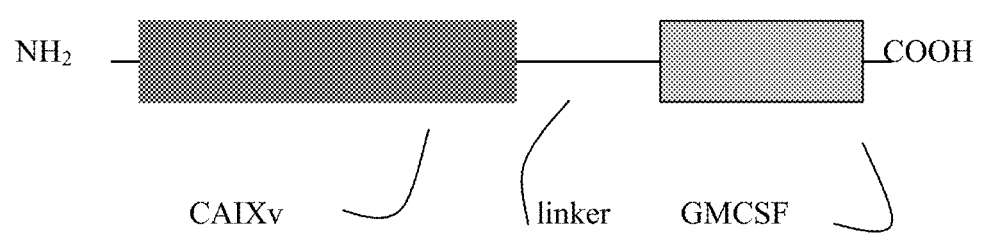

NH₂ —■■■■■■■■■— ▨▨▨▨— COOH

CAIXv     linker   GMCSF

US 9,968,664 B2

FUSION MOLECULE BASED ON NOVEL TAA VARIANT

CROSS-REFERENCES TO RELATED APPLICATIONS

This application is a continuation of U.S. application Ser. No. 15/073,162, filed Mar. 17, 2016, now U.S. Pat. No. 9,492,520, which is a divisional of U.S. application Ser. No. 13/740,099, filed Jan. 11, 2013, now U.S. Pat. No. 9,322,010, which is a continuation of U.S. application Ser. No. 12/520,084, filed Feb. 26, 2010, now U.S. Pat. No. 8,378,084, which is a National Stage application under 35 U.S.C. § 371 of PCT/US2007/088676, filed Dec. 21, 2007, which is an application claiming benefit under 35 U.S.C. § 119(e) of U.S. Provisional Application Ser. No. 60/876,863, filed Dec. 22, 2006, each of which is incorporated herein by reference in its entirety.

REFERENCE TO A SEQUENCE LISTING," A TABLE, OR A COMPUTER PROGRAM LISTING APPENDIX SUBMITTED AS AN ASCII TEXT FILE

The Sequence Listing written in file SequenceListing_079822-1024479.txt, created on Oct. 12, 2016, 20,679 bytes, machine format IBM-PC, MS-Windows operating system, is hereby incorporated by reference in its entirety for all purposes.

FIELD OF THE INVENTION

The present invention generally relates to the science of oncology and tumor associated antigens. More specifically, the invention provides novel carbonic anhydrase IX (CAIX) nucleic acid and peptide sequences, as well as related compositions and methods.

BACKGROUND OF THE INVENTION

Renal cell carcinoma (RCC) affects approximately 39,000 Americans and causes an estimated 13,000 deaths per year. Approximately one third of RCC patients will have advanced disease at presentation, and one third of patients with localized disease will eventually progress to metastatic disease. Of late, much progress and intensive research efforts have been made in RCC therapies. Metastatic RCC poses a therapeutic challenge because of its resistance to conventional modes of therapy, such as chemotherapy and radiation therapy, and considerable hurdles to eliciting an effective immune response for eradication of the remaining cancer cells (owing, at least in part, to their high invasion and metastatic potential).

Recent advances in the better understanding of molecular pathogenesis of RCC has led to the development of several novel agents and approaches including immunotherapy and gene therapy, which have been applied in clinical trials with RCC patients. However, the treatments for advanced stages of RCC patients have been modest despite the considerable research efforts in this direction and the majority of patients ultimately succumbed to the disease. The long-term survival for patients with metastatic RCC remains only 10-20%.

Although the ability of cytotoxic T cell to recognize post-translationally modified epitopes has been acknowledged for several years, few have exploited this observation in a targeted approach to generate immune responses of therapeutic benefit. Therefore, the success of cancer immunotherapy has focused on the identification of tumor-associated antigen (TAAs), which ideally are expressed exclusively by the cancer cells and not by normal adult tissues.

An exemplary TAA is carbonic anhydrase IX (CAIX), a transmembrane enzyme that regulates intracellular and extracellular pH during periods of hypoxia by catalyzing the interconversion between $CO_2$ and bicarbonate. This cell surface protein may also be involved in oncogenesis and tumor progression, and is thought to play a role in regulating cellular proliferation and possibly cellular adhesion.

New markers that correlate with clinical outcome or identify patients with potentially aggressive disease, such as the novel CAIX variant provided herein, can dramatically improve the diagnosis and management of RCC. The present application accordingly provides a CAIX variant with novel cDNA and amino acidic sequences. These sequences differ from the CAIX sequences reported thus far (e.g., sequences in NCBI Gene/protein database and UniProtKB/Swiss-Prot protein database). In addition, the invention provides fusion/chimeric molecules (e.g., GMCSF-CAIXv) and antibodies based on this newly identified CAIX variant. The CAIXv nucleic acids, polypeptides, and related constructs find use in the treatment and diagnosis of cancer.

SUMMARY OF THE INVENTION

In a first aspect, a polypeptide comprising SEQ ID NO: 1 or a portion thereof having at least 20 contiguous amino acids of SEQ ID NO:1 and including one or more of residues M33, G121, and S374 is provided. Also provided is an isolated or recombinant nucleic acid comprising a polynucleotide sequence selected from the group consisting of (a) SEQ ID NO: 2; (b) a polynucleotide sequence encoding a polypeptide comprising SEQ ID NO: 1; and, (c) a polynucleotide sequence comprising a fragment of (a) or (b), which fragment encodes at least 20 contiguous amino acids of SEQ ID NO:1 and comprises one or more of residues M33, G121 and S374.

A further embodiment of the present invention provides methods of aiding in a cancer prognosis. The method include the steps of (a) quantifying expressed novel CAIX variant, if any, present in one or more samples derived from a subject diagnosed with cancer to produce quantified novel CAIX variant expression data, wherein the expressed novel CAIX variant comprises SEQ ID NO: 1, a portion of SEQ ID NO:1 comprising one or more of residues M33, G121 and S374, or a nucleic acid encoding the novel CAIX variant or portion thereof; and, (b) correlating the quantified novel CAIX variant expression data with a probability of a cancer prognosis for the subject. Cancers for which prognoses can be determined using the methods of the claimed invention include, but are not limited to, renal clear cell carcinoma, cervical cancer, bladder cancer, and hypoxia-inducible cancer.

In an additional embodiment of the present invention, methods of aiding in a cancer prognosis comprising the steps of (a) quantifying expressed novel CAIX variant polypeptides, if any, present in one or more samples derived from a subject diagnosed with a cancer that expresses CAIX to produce quantified CAIX polypeptide expression data, wherein the samples are derived from a tumor and/or a metastatic lesion derived from a tumor; and, (b) correlating the quantified novel CAIX variant polypeptide expression data with a probability of a cancer prognosis, wherein a quantification percentage of 85% stratifies the prognosis for the subject. Optionally, the quantified CAIX expression data are in a computer-readable form, and wherein (b) comprises operating a programmable computer that comprises at least one database and executing an algorithm that determines closeness-of-fit between the computer-readable quantified CAIX expression data and database entries, which entries correspond to clinical and/or pathological data for a population of cancer patients to thereby correlate the quantified CAIX expression data with the probability of the cancer prognosis for the subject.

The present invention also provides constructs comprising a portion of novel CAIX variant (SEQ ID NO: 1) coupled to a granulocyte macrophage colony stimulating factor (GM-CSF) or other immuno-effector or cytokine, wherein the portion of novel CAIX variant comprises one or more of residues M33, G121 and/or S374. Optionally, the construct is part of a composition having a pharmaceutically acceptable diluent, excipient, and/or adjuvant. Accordingly, a CAIXv according to the invention contains the substitutions D33M, D121G, or N364S with respect to the CAIX protein.

In a further aspect, the present invention provides nucleic acids encoding a fusion protein comprising a portion of novel CAIX variant (SEQ ID NO: 1) attached to a granulocyte macrophage colony stimulating factor (GM-CSF) or a cytokine or immuno-effector, wherein the portion of novel CAIX variant comprises one or more of residues M33, G121 and S374. Optionally, the nucleic acid is provided as an expression cassette or in a vector. The present invention also includes host cells transfected with said nucleic acid.

In an additional embodiment, the present invention provides methods of producing an anti-tumor vaccine, including the steps of culturing a cell transfected with a nucleic acid encoding a cytokine-CAIX fusion protein, under conditions where said cell expresses the fusion protein; and recovering said fusion protein.

In a further aspect, the present invention provides methods of inducing an immune response against a CAIX antigen. The method includes the steps of activating a cell of the immune system with a construct comprising a portion of novel CAIX variant (which portion comprises one or more of residues M33, G121 and S374 of SEQ ID NO: 1) coupled to a cytokine, (e.g., granulocyte macrophage colony stimulating factor) or other immuno-effector, whereby said activating provides an immune response directed against the novel CAIX variant. The activating step can comprise contacting an antigen presenting cell with said construct. Alternatively, activation of the immune system cell can be achieved by injecting the construct into an animal (e.g., a mammal).

Suitable cytokines for use in any of the above embodiments are mammalian (preferably, human) cytokines, including but not limited to those selected from the group consisting of interferons (IFNs) (e.g., IFN-α, IFN-γ), interleukins 1 to 20 (e.g., IL-2, IL-4, IL-6), and TNF. It is contemplated that such cytokines may be employed in constructs and methods generally as exemplified further below with GMCSF.

In an additional embodiment of the present invention, methods of inhibiting the proliferation or growth of a transformed cell that bears a novel CAIX variant are provided. The methods include removing or obtaining an immune cell from a mammalian host; activating said immune cell by contacting said cell with a protein comprising the novel CAIX variant (SEQ ID NO: 1 or a fragment thereof comprising one or more of residues M33, G121 and S374), wherein the novel CAIX variant or fragment thereof is attached to a cytokine (e.g., granulocyte macrophage colony stimulating factor (GM-CSF) or a fragment thereof); optionally expanding the activated cell; and infusing the activated cell into an organism containing a transformed cell bearing the novel CAIX variant, thereby inhibiting the growth of the transformed cell. The immune cell can be, for example, peripheral blood lymphocytes (PBLs) or tumor infiltrating lymphocytes (TILs) from the mammalian host; optionally, the immune cell thus obtained and activated is infused back into the source host. Immune cells that can be employed in the methods of the present invention include, but are not limited to, dendritic cells, antigen presenting cells, B lymphocytes, T-cells, and a tumor infiltrating lymphocytes.

A further embodiment of the present invention provides methods of treating an individual having a cancer characterized by an altered expression of CAIX or CAIXv. The methods include the steps of (a) sensitizing antigen presenting cells in vitro with a sensitizing-effective amount of a chimeric fusion protein comprising the novel CAIX variant attached to a granulocyte macrophage colony stimulating factor (GM-CSF) or other cytokine, wherein the novel CAIX variant comprises SEQ ID NO: 1 or a fragment of at least 20 contiguous amino acids of SEQ ID NO:1 and includes one or more of residues M33, G121, and S374; and (b) administering to an individual having said cancer or metastasis a therapeutically effective amount of the sensitized antigen presenting cells. The antigen presenting cells can be autologous to the individual, or are MHC matched allogenic dendritic cells. Any of a number of cells (e.g., peripheral blood lymphocytes, monocytes, fibroblasts, TILs, and/or dendritic cells) by contacting the cells with said chimeric fusion protein. In a preferred embodiment, the sensitizing step comprises transfecting dendritic cells or RCCs with a nucleic acid encoding said chimeric fusion protein. The CAIXv cell surface protein is thought to be involved in oncogenesis and tumor progression, and in regulating cellular proliferation and possibly cellular adhesion. CAIX and CAIXv is inducible by hypoxia, a state found in many cancers and accordingly all tumors can be targeted by the methods of the invention. I As CAIX and CAIXv is inducible by hypoxia, a state found in many cancers, accordingly all tumors, (e.g., all solid tumors) can be targeted by the methods of the invention. In some embodiments of any of the above, the cancer is cervical cancer, bladder cancer, or renal cancer.

In another aspect, the invention provides antibodies which are specific to a CAIXv polypeptide. These antibodies typically would have at least an affinity for a CAIXv of $10^{-5}$ M or, more preferably, at least of $10^{-6}$ M or $10^{-7}$ M. In some further embodiments, these antibodies bind to a portion of SEQ ID NO:1 comprising one, two or three of residues M33, G121 and S374. Preferably, these antibodies are selective in binding to a CAIXv comprising one or more of residues M33, G121 and S374, as compared to the human CAIX protein of SEQ ID NO:3 or as disclosed in U.S. patent application Ser. No. 10/511,465 to Bui et al. and related PCT application PCT/US2003/11561. For instance, the antibody can be selective in binding to a CAIXv comprising one or more of residues M33, G121 and S374, as compared to a CAIX protein having the sequence of SEQ ID NO:3 or another amino acid sequence at those particular positions. The relative binding affinity for a selective antibody can be at least 5-fold or 10-different. These antibodies are also contemplated for use in the methods according to the invention.

These and a variety of additional features of the present invention will become evident upon review of the following disclosure.

BRIEF DESCRIPTION OF THE DRAWINGS

FIG. 1. A schematic representation of a CAIXv construct according to the invention. The FIGURE shows an N-terminal CAIXv linked via a linker to a carboxy terminal GMCSF polypeptide.

DETAILED DESCRIPTION OF THE INVENTION

The present application accordingly provides a CAIX variant with novel cDNA and amino acidic sequences. These sequences differ from the CAIX sequences reported thus far (e.g., sequences in NCBI Gene/protein database and UniProtKB/Swiss-Prot protein database). The sequences come from fresh kidney cells obtained from human patients. In addition, the invention provides fusion/chimeric molecules (e.g., GMCSF-CAIXv) based on this newly identified CAIX variant. The invention also provides CAIXv nucleic acids, polypeptides, and related constructs which find use in the treatment and diagnosis of cancer.

This invention provides a novel approach to the treatment of renal cell carcinomas, cervical cancers, and bladder cancers. In particular this invention pertains to the discovery that a chimeric molecule comprising a granulocyte macrophage colony stimulating factor (GM-CSF) attached to a CAIXv kidney cancer specific antigen provides a highly effective "vaccine" that raises an immune response directed against renal cell cancers. The chimeric molecule can be used as a traditional vaccine or in adoptive immunotherapeutic applications. Nucleic acids encoding a GM-CSF-CAIXv fusion protein can be used as naked DNA vaccines or to transfect cell in an adoptive immunotherapeutic treatment regimen.

Thus in one embodiment, this invention provides a construct comprising a CAIXv polypeptide attached to a granulocyte macrophage colony stimulating factor (GM-CSF) or other cytokine or immuno-effector. The GM-CSF is preferably a human GM-CSF, or a biologically active fragment and/or mutant thereof. Similarly the CAIXv polypeptide is a preferably a human CAIXv polypeptide. In particularly preferred embodiments the CAIXv polypeptide is covalently attached to the GM-CSF (directly or through a linker). A suitable linker is encoded by the nucleotide sequence AAGCTT which encodes -Lys-Leu-. In a particularly preferred embodiment the CAIXv and the GM-CSF are components of a fusion protein (chemically constructed or recombinantly expressed. In such fusion proteins, the CAIXv polypeptide and the GM-CSF are directly joined, or more preferably, joined by a peptide linker ranging in length from 2 to about 50, more preferably from about 2 to about 20, and most preferably from about 2 to about 10 amino acids. One preferred peptide linker is -Lys-Leu-. A particularly preferred construct has a CAIXv of SEQ ID NO: 1.

Suitable cytokines for use in any of the above embodiments are mammalian (preferably, human) cytokines, including but not limited to those selected from the group consisting of interferons (IFNs) (e.g., IFN-α, IFN-γ), interleukins 1 to 20 (e.g., IL-2, IL-4, IL-6), and TNF. It is contemplated that such cytokines may be employed in constructs and methods generally as exemplified further below with GMCSF. Accordingly, in some embodiments, the GM-CSF of a construct described below is replaced by a cytokine selected from the group consisting of interferons (IFNs) (e.g., IFN-α, IFN-γ), interleukins 1 to 20 (e.g., IL-2, IL-4, IL-6), and TNF. In some embodiments, one or more cytokines are fused to the CAIXv.

In another embodiment this invention provides a composition comprising the chimeric molecules described herein and a pharmaceutically acceptable diluent or excipient.

This invention also provides a nucleic acid (e.g. a DNA or an RNA) encoding a fusion protein comprising a CAIXv kidney cancer specific polypeptide or antigen attached to a granulocyte macrophage colony stimulating factor (GM-CSF). The CAIXv can be an antigenic fragment or cancer-specific epitope of CAIXv. Similarly the GM-CSF is a preferably a human GM-CSF or a biologically active fragment thereof. In one preferred embodiment the nucleic acid encodes a fusion protein where the CAIXv and the GM-CSF are directly joined, or more preferably, joined by a peptide linker ranging in length from 2 to about 50, more preferably from about 2 to about 20, and most preferably from about 2 to about 10 amino acids. In certain embodiments, the nucleic acid may preferably encode a linker that is -Arg-Arg-. One preferred nucleic acid is the nucleic acid of SEQ ID NO: 2. In some preferred embodiments, the nucleic acid is a nucleic acid that encodes the polypeptide of SEQ ID NO: 1. The nucleic acid is preferably in an expression cassette and in certain embodiments, the nucleic acid is present in a vector (e.g. a baculoviral vector).

This invention also provides a host cell transfected with one or more of the nucleic acids described herein. The host cell is preferably a eukaryotic cell, and most preferably an insect cell.

This invention also provides methods of producing an anti-tumor vaccine. The methods preferably involve culturing a cell transfected with a nucleic acid encoding a chimeric GM-CSF-CAIXv chimeric molecule under conditions where the nucleic expresses a CAIXv-GM-CSF fusion protein and recovering said fusion protein. Again the cell is preferably a eukaryotic cell, more preferably an insect (e.g. an SF9) cell.

In another embodiment, this invention provides methods of inducing an immune response against the CAIXv kidney cancer-specific antigen, and/or a cell displaying the CAIXv kidney cancer-specific antigen, and/or any cancer cell that expresses a CAIXv antigen, and/or an antigen cross-reactive with a CAIXv antigen. The methods involve activating a cell of the immune system with a construct comprising a kidney cancer specific antigen (CAIXv) attached to a granulocyte macrophage colony stimulating factor (GM-CSF) whereby the activating provides an immune response directed against the CAIXv antigen. In some embodiments, the activating comprises contacting an antigen presenting cell (e.g. monocyte, or dendritic cell) with the construct (chimeric molecule). In certain embodiments, the activated cell is a cytotoxic T-lymphocyte (CTL), or a tumor infiltrating lymphocyte, etc. The activating can also involve contacting a peripheral blood lymphocyte (PBL) or a tumor infiltrating lymphocyte (TIL) with the construct. The contacting can take place in vivo, or ex vivo (e.g., in vitro). In various embodiments, the activating comprises loading an antigen presenting cell (APC) with a polypeptide comprising a CAIXv. The activation can also comprise transfecting a cell (e.g., a PBL, an APC, a TIL, a renal cell carcinoma tumor cell, etc.) with a nucleic acid encoding a GM-CSF-CAIXv fusion protein. The method may further comprise infusing cells (e.g. cytotoxic T lymphocytes) back into the mammal.

In still another embodiment this invention provides a method of inhibiting the proliferation or growth of a transformed (e.g. neoplastic) kidney cell. The method involves activating a cell of the immune system with a construct comprising a kidney cancer specific antigen (CAIXv) attached to a granulocyte macrophage colony stimulating factor (GM-CSF) whereby the activating provides an immune response directed against the CAIXv antigen and the immune response inhibits the growth or proliferation of a transformed kidney cancer cell. In preferred embodiments, the transformed kidney cancer cell is a renal cell carcinoma cell (e.g. in a solid tumor, a disperse tumor, or a metastatic tumor). The activating can comprise contacting an antigen presenting cell (e.g. a dendritic cell) with the construct. The activated cell can include, but is not limited to a cytotoxic T-lymphocyte (CTL) a tumor infiltrating lymphocyte (TIL), etc. In certain embodiments, the activating comprises injecting (or otherwise administering) to a mammal one or more of the following: a polypeptide comprising a GM-CSF-CAIXv fusion protein; dendritic cells pulsed with a GM-CSF-CAIXv fusion protein; a gene therapy construct (e.g. adenovirus, gutless-adenovirus, retrovirus, lentivirus, adeno-associated virus, vaccinia virus, simian virus 40, etc) comprising a nucleic acid encoding a GM-CSF-CAIXv fusion protein, a dendritic expressing a GM-CSF-CAIXv fusion protein, a tumor cell (e.g. RCC) expressing a GM-CSF-CAIXv fusion protein, a fibroblast expressing a GM-CSF-CAIXv fusion protein, a GM-CSF-CAIXv naked DNA, a transfection reagent (e.g. cationic lipid, dendrimer, liposome, etc. containing or complexed with a nucleic acid encoding a GM-CSF-CAIXv polypeptide. In a particularly preferred embodiment, activating comprises activating isolated dendritic cells/PMBCs. In another embodiment, the activating comprises contacting (in vivo or ex vivo) a peripheral blood lymphocyte (PBL) or a tumor infiltrating lymphocyte (TIL) with said construct. The peripheral blood cells and/or dendritic cells and/or monocytes are preferably infused into the subject.

This invention also provides a method of inhibiting the proliferation or growth of a transformed renal carcinoma cell (RCC) that bears a CAIXv antigen. The method involves removing an immune cell from a mammalian host; activating the immune cell by contacting the cell with a protein comprising a renal cell carcinoma specific antigen (CAIXv) attached to a granulocyte macrophage colony stimulating factor (GM-CSF) or a fragment thereof, optionally expanding the activated cell; and infusing the activated cell into an organism containing a transformed renal cell carcinoma bearing a CAIXv. In certain embodiments, the activating comprises contacting the cell with one or more of the following: a polypeptide comprising a GM-CSF-CAIXv fusion protein; dendritic cells pulsed with a GM-CSF-CAIXv fusion protein; a gene therapy construct (e.g. adenovirus, gutless-adenovirus, retrovirus, lantivirus, adeno-associated virus, vaccinia virus, simian virus 40, etc) comprising a nucleic acid encoding a GM-CSF-CAIXv fusion protein, a dendritic expressing a GM-CSF-CAIXv fusion protein, a tumor cell (e.g. RCC) expressing a GM-CSF-CAIXv fusion protein, a fibroblast expressing a GM-CSF-CAIXv fusion protein, a GM-CSF-CAIXv naked DNA, a transfection reagent (e.g. cationic lipid, dendrimer, liposome, etc. containing or complexed with a nucleic acid encoding a GM-CSF-CAIXv polypeptide. In a particularly preferred embodiment, activating comprises activating isolated dendritic cells/PMBCs. In another embodiment, the activating comprises contacting (in vivo or ex vivo) a peripheral blood lymphocyte (PBL) or a tumor infiltrating lymphocyte (TIL) with said construct. The peripheral blood cells and/or dendritic cells and/or monocytes are preferably infused into the subject. The removing may comprise isolating and culturing peripheral blood lymphocytes and/or monocytes, and/or dendritic cells from the mammalian host. The infusing may involve infusing the cultured cells or activated cells produced using the cultured cells into the host from which the immune cell was removed.

In still another embodiment, this invention provides a method of treating an individual having a renal cell cancer. The method involves sensitizing antigen presenting cells (e.g., PBMCs, dendritic cells, etc.) in vitro with a sensitizing-effective amount of a chimeric fusion protein comprising a renal cell carcinoma specific antigen (CAIXv) attached to a granulocyte macrophage colony stimulating factor (GM-CSF); and administering to an individual having said renal cell cancer or metastasis a therapeutically effective amount of the sensitized antigen presenting cells. In particularly preferred embodiments, the antigen presenting cells are autologous to the individual or allogenic with matched MHC. In certain embodiments, the sensitizing involves contacting peripheral blood lymphocytes or monocytes or dendritic cells with CAIXv-GM-CSF fusion protein. In certain embodiments, the sensitizing involves contacting PBL, TIL, monocyte, dendritic cell with a CAIXv-GM-CSF polypeptide and/or transfecting dendritic cell, APC, RCC, fibroblasts, with a nucleic acid encoding the chimeric fusion protein.

In some embodiments according to the invention, the patient or subject is a mammal selected from the group consisting of a human, a non-human primate, a rodent, a porcine, a largomorph, a canine, a feline, an equine, a porcine, and a bovine.

Definitions

Unless defined otherwise, all technical and scientific terms used herein have the same meaning as commonly understood by one of ordinary skill in the art to which, the invention pertains. Although any methods and materials similar or equivalent to those described herein can be used in the practice for testing of the present invention, the preferred materials and methods are described herein. In describing and claiming the present invention, the following terminology will be used in accordance with the definitions set out below.

As used in this specification and the appended claims, the singular forms "a", "an" and "the" include plural referents unless the content clearly dictates otherwise. Thus, for example, reference to "a surface" includes a combination of two or more surfaces; reference to "bacteria" includes mixtures of bacteria, and the like.

The terms "carbonic anhydrase IX" and "CAIX" are herein considered to be synonymous with "CA9", "MN", and "G250." The G250 antigen has been sequenced and revealed by database analysis to be homologous to the MN/CAIX antigen, a tumor-associated antigen originally identified in HeLa cells (Pastorek et al. (1994) "Cloning and characterization of MN, a human tumor associated protein with a domain homologous to carbonic anhydrase and a putative helix-loop-helix DNA binding segment," *Oncogene* 9:2877-2888 and Oosterwijk et al. (1996) "Molecular characterization of the renal cell carcinoma associated antigen G250," *Proc Amer Assoc Cancer Res* 37:461). This antigen (MN/CAIX/CA9/G250) is a plasma membrane glycoprotein with an apparent molecular weight of 54/58 kDa, detectable in several types of malignancies; e.g. cervical and ovarian cancer (Liao et al. et al. (1994) "Identification of the MN antigen as a diagnostic biomarker of cervical intraepithelial squamous and glandular neoplasia and cervical carcinomas," *Am J Pathol* 145:598-609), renal cancer (Oosterwijk et al. (1986) "Immunohistochemical analysis of monoclonal antibodies to renal antigens," *Am J Pathol* 123:301-309), colorectal cancer (Saarnio et al. (1997) "Immunohistochemical study of colorectal tumors for expression of a novel transmembrane carbonic anhydrase, MN/CA IX, with potential value as a marker of cell proliferation," *Am J Pathol* 153:279-285), esophageal cancer (Turner et al. (1997) "MN antigen expression in normal, preneoplastic, and neoplastic esophagus: a clinicopathological study of a new cancer-associated biomarker," *Human Pathol* 28:740-744), bladder cancer (Uemura et al. (1997) "Expression of tumor-associated antigen MN/G250 in urologic carcinoma: potential therapeutic target," *J Urol* (Suppl) 157:377), but not in the normal tissues except alimentary tract, which indicates that the CAIX protein is associated with tumorigenicity. Sequential analysis has demonstrated that the gene (MN/CAIX/CA9/G250) is a novel member of the carbonic anhydrase (CA) family and MN/CADUG250 is considered to be the only tumor-associated CA isoenzyme. See, e.g., U.S. Pat. No. 6,297,051, entitled "MN GENE AND PROTEIN" issued Oct. 2, 2001 to Zavada et al., which is incorporated by reference in its entirety for all purposes.

Carbonic anhydrase IX (CAIX) is a cell surface tumor-associated antigen that is highly expressed and used as a molecular signature for most RCCs. As such, CAIX has been an attractive biomarker for the development of CAIX targeted therapeutic interventions and diagnostics. U.S. patent application Ser. No. 10/511,465 to Bui et al. and related PCT application PCT/US2003/11561, which are incorporated herein by reference in their entirety, provides methods of using CAIX as a molecular marker associated with RCC disease progression and survival before. The level of expression of the molecular biomarker, reflected by its immunochemical staining profile, correlated with response to treatment, clinical factors, pathological features and survival. In addition, U.S. patent application Ser. No. 09/783,708 to Belldegrun et al., also incorporated herein by reference in its entirety, describes methods for treatment (e.g. mitigation of symptoms) of cancers that express CAIX, or an antigen cross-reactive with CAIX.

The cDNA and amino acidic sequences of CAIX as reported in NCBI Gene/protein database (and used in laboratories around the world) stemmed from cancer cell lines propagated in cell cultures system. In contrast, the novel CAIX variant provided herein were identified directly from RCC tumor patients' tissues via RT-PCR and sequence analysis. Surprisingly, the CAIX sequence obtained from tissue differs from the CAIX sequences derived from cell culture system and reported in other laboratories. In particular, we have found there are two or three amino acids that vary from all of the reported CAIX amino acidic sequences in NCBI gene/protein database and UniProtKB/Swiss-Prot protein sequence database, respectively. As such, the novel CAIX sequences provided herein, which reflect the protein present in situ (e.g., in CAIX-expressing cancer tissues), provides novel biomarker that can be employed for identifying, improving and managing the therapeutic outcomes in patients having CAIX-expressing cancers, such as metastatic RCC patients.

The novel CAIXv sequences are as follows:

TABLE 1

CAIX Protein Sequence (SEQ ID NO: 1):

MAPLCPSPWLPLLIPAPAPGLTVQLLLSLLLLMPVHPQRLPRMQEDSPLG

GGSSGEDDPLGEEDLPSEEDSPREEDPPGEEDLPGEEDLPEVKP

TABLE 1-continued

CAIX Protein Sequence (SEQ ID NO: 1):

KSEEEGSLKLEDLPTVEAPGGPQEPQNNAHRDKEGDDQSHWRYGGDPPWP

RVSPACAGRFQSPVDIRPQLAAFCPALRPLELLGFQLPPLPELRLRNNGH

SVQLTLPPGLEMALGPGREYRALQLHLHWGAAGRPGSEHTVEGHRFPAEI

HVVHLSTAFARVDEALGRPGGLAVLAAFLEEGPEENSAYEQLLSRLEEIA

EEGSETQVPGLDISALLPSDFSRYFQYEGSLTTPPCAQGVIWTVFNQTVM

LSAKQLHTLSDTLWGPGDSRLQLSFRATQPLNGRVIEASFPAGVDSSPRA

AEPVQLNSCLAAGDILALVFGLLFAVTSVAFLVQMRRQHRRGTKGGVSYR

PAEVAETGA

TABLE 2

CAIXv cDNA Sequence (SEQ ID NO: 2):

ATGGCTCCCCTGTGCCCCAGCCCCTGGCTCCCTCTGTTGATCCCGGCCCC

TGCTCCAGGCCTCACTGTGCAACTGCTGCTGTCACTGCTGCTTCTGATGC

CTGTCCATCCCCAGAGGTTGCCCCGGATGCAGGAGGATTCCCCCTTGGGA

GGAGGCTCTTCTGGGGAAGATGACCCACTGGGCGAGGAGGATCTGCCCAG

TGAAGAGGATTCGCCCAGAGAGGAGGATCCACCCGGAGAGGAGGATCTAC

CTGGAGAGGAGGATCTACCTGGAGAGGAGGATCTACCTGAAGTTAAGCCT

AAATCAGAAGAAGAGGGCTCCCTGAAGTTAGAGGATCTACCTACCGTTGA

GGCTCCTGGAGGTCCTCAAGAACCCCAGAATAATGCCCACAGGGACAAAG

AAGGGGATGACCAGAGTCATTGGCGCTATGGAGGCGACCCGCCCTGGCCC

CGGGTGTCCCCAGCCTGCGCGGGCCGCTTCCAGTCCCCGGTGGATATCCG

CCCCCAGCTCGCCGCCTTCTGCCCGGCCCTGCGCCCCCTGGAACTCCTGG

GCTTCCAGCTCCCGCCGCTCCCAGAACTGCGCCTGCGCAACAATGGCCAC

AGTGTGCAACTGACCCTGCCTCCTGGGCTAGAGATGGCTCTGGGTCCCGG

GCGGGAGTACCGGGCTCTGCAGCTGCATCTGCACTGGGGGGCTGCAGGTC

GTCCGGGCTCGGAGCACACTGTGGAAGGCCACCGTTTCCCTGCCGAGATC

CACGTGGTTCACCTCAGCACCGCCTTTGCCAGAGTTGACGAGGCCTTGGG

GCGCCCGGGAGGCCTGGCCGTGTTGGCCGCCTTTCTGGAGGAGGGCCCGG

AAGAAAACAGTGCCTATGAGCAGTTGCTGTCTCGCTTGGAAGAAATCGCT

GAGGAAGGCTCAGAGACTCAGGTCCCAGGACTGGACATATCTGCACTCCT

GCCCTCTGACTTCAGCCGCTACTTCCAATATGAGGGGTCTCTGACTACAC

CGCCCTGTGCCCAGGGTGTCATCTGGACTGTGTTTAACCAGACAGTAATG

CTGAGTGCTAAGCAGCTCCACACCCTCTCTGACACCCTGTGGGGACCCGG

TGACTCTCGGCTACAACTGAGCTTCCGAGCGACGCAGCCTTTGAATGGGC

GAGTGATTGAGGCCTCCTTCCCTGCTGGAGTGGACAGCAGTCCTCGGGCT

GCTGAGCCAGTCCAGCTGAATTCCTGCCTGGCTGCTGGTGACATTCTAGC

CCTGGTTTTTGGCCTCCTTTTTGCTGTCACCAGCGTCGCGTTCCTTGTGC

TABLE 2-continued

CAIXv cDNA Sequence (SEQ ID NO: 2):

AGATGAGAAGGCAGCACAGAAGGGGAACCAAAGGGGTGTGAGCTACCGC

CCAGCAGAGGTAGCCGAGACTGGAGCCTAG

The term "CAIX variant" or "CAIXv" references a polypeptide of SEQ ID NO:1 or a portion of the polypeptide or a portion thereof, wherein the portion comprises at least 20 contiguous amino acids of SEQ ID NO:1 and includes one or more of residues M33, G121, and S374. In some embodiments, the polypeptide comprises the full polypeptide sequence of SEQ ID NO:1. In other embodiments, the portion comprises at least 20, 30, 40, 50, 60, 70, 100, 200 or 300 contiguous amino acids. In some embodiments, the portion comprises M33, G121, or S374.

A CAIXv-GM-CSF construct or GM-CSF-CAIXv construct reference a chimeric molecule comprising a CAIX variant attached to a granulocyte-macrophage colony stimulating factor. The attachment may be a chemical conjugation (direct or through a linker) or the chimeric molecule can be a fusion protein (recombinantly expressed or assembled by condensation of the two subject molecules). Accordingly, the notation "CAIXv-GM-CSF" or "GM-CSF-CAIXv" encompasses embodiments where the CAIXv and the GM-CSF are attached terminally or to an internal site and contemplates attachment of the CAIXv to either the amino or carboxyl terminus of the GM-CSF. In addition, the term CAIXv-GMCSF may encompass chimeric molecules comprising fragments of CAIXv wherein the CAIXv fragments retain the epitope recognized by antibodies that specifically target renal cell carcinomas bearing the CAIXv protein or antigen. Similarly, the term may encompass chimeric molecules comprising fragments of GM-CSF where the GM-CSF retain the biological activity of native GM-CSF (e.g. are recognized by receptors that recognize native GM-CSF and/or show similar mitogenic activity, etc.). In some embodiments, the GM-CSF is human GM-CSF. The above CAIXv polypeptides can be used in the methods and constructs of the invention.

The term "CAIXv nucleic acid" references a nucleic acid which encodes a CAIXv polypeptide. In one embodiment, the CAIXv nucleic acid sequence is SEQ ID NO:2. A CAIXv nucleic acid can be or comprise a polynucleotide sequence selected from the group consisting of (a) SEQ ID NO: 2; (b) a polynucleotide sequence encoding a polypeptide comprising SEQ ID NO: 1; and, (c) a polynucleotide sequence comprising a fragment of (a) or (b), which fragment encodes at least 20 contiguous amino acids of SEQ ID NO:1 and comprises one or more of residues M33, G121 and S374. The above CAIXv nucleic acids are suitable for use in the methods and constructs of the invention.

"Renal cell carcinoma" or "RCC" refers to carcinoma of the renal parenchyma. RCC is also often identified as renal cancer, "hypernephroma", or adenocarcinoma of the kidney. There are four main types of renal cell carcinoma, namely, clear cell type, granular cell type, mixed granular and clear cell type, and spindle cell type.

The terms "polypeptide", "peptide", and "protein" are used interchangeably herein to refer to a polymer of amino acids that are covalently bound by peptide linkages. The terms "polypeptide", "peptide", and "protein" include glycoproteins as well as non-glycoproteins.

The terms "nucleic acid" or "oligonucleotide" or grammatical equivalents herein refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) Tetrahedron 49(10):1925) and references therein; Letsinger (1970) J. Org. Chem. 35:3800; Sprinzl et al. (1977) Eur. J. Biochem. 81: 579; Letsinger et al. (1986) Nucl. Acids Res. 14: 3487; Sawai et al. (1984) Chem. Lett. 805, Letsinger et al. (1988) J. Am. Chem. Soc. 110: 4470; and Pauwels et al. (1986) Chemica Scripta 26: 1419), phosphorothioate (Mag et al. (1991) Nucleic Acids Res. 19:1437; and U.S. Pat. No. 5,644,048), phosphorodithioate (Briu et al. (1989) J. Am. Chem. Soc. 111:2321, O-methylphophoroamidite linkages (see Eckstein, Oligonucleotides and Analogues: A Practical Approach, Oxford University Press), and peptide nucleic acid backbones and linkages (see Egholm (1992) J. Am. Chem. Soc. 114:1895; Meier et al. (1992) Chem. Int. Ed. Engl. 31: 1008; Nielsen (1993) Nature, 365: 566; Carlsson et al. (1996) Nature 380: 207). Other analog nucleic acids include those with positive backbones (Denpcy et al. (1995) Proc. Natl. Acad. Sci. USA 92: 6097; non-ionic backbones (U.S. Pat. Nos. 5,386,023, 5,637,684, 5,602,240, 5,216,141 and 4,469,863; Angew. (1991) Chem. Intl. Ed. English 30: 423; Letsinger et al. (1988) J. Am. Chem. Soc. 110:4470; Letsinger et al. (1994) Nucleoside & Nucleotide 13:1597; Chapters 2 and 3, ASC Symposium Series 580, "Carbohydrate Modifications in Antisense Research", Ed. Y. S. Sanghui and P. Dan Cook; Mesmaeker et al. (1994), Bioorganic & Medicinal Chem. Lett. 4: 395; Jeffs et al. (1994) J. Biomolecular NMR 34:17; Tetrahedron Lett. 37:743 (1996)) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghui and P. Dan Cook. Nucleic acids containing one or more carbocyclic sugars are also included within the definition of nucleic acids (see Jenkins et al. (1995), Chem. Soc. Rev. pp 169-176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments.

The term "immune cell" refers to a cell that is capable of participating, directly or indirectly, in an immune response. Immune cells include, but are not limited to T-cells, B-cells, dendritic cells, cytotoxic T-cells, tumor infiltrating lymphocytes, etc.

As used herein, the term "activating" (e.g. as in activating a cell or activating an immune response) includes direct activation as by contact with the construct or by indirect activation as by contact with the construct or antigenic fragment via an antigen presenting cell (e.g. a dendritic cell).

A "fusion protein" refers to a polypeptide formed by the joining of two or more polypeptides through a peptide bond formed between the amino terminus of one polypeptide and the carboxyl terminus of another polypeptide. The fusion protein may be formed by the chemical coupling of the constituent polypeptides, or it may be expressed as a single polypeptide from nucleic acid sequence encoding the single contiguous fusion protein. A single chain fusion protein is a fusion protein having a single contiguous polypeptide backbone.

A "spacer" or "linker" as used in reference to a fusion protein refers to a peptide that joins the proteins comprising a fusion protein. Generally a spacer has no specific biological activity other than to join the proteins or to preserve some minimum distance or other spatial relationship between them. However, the constituent amino acids of a spacer may be selected to influence some property of the molecule such as the folding, net charge, or hydrophobicity of the molecule.

A "spacer" or "linker" as used in reference to a chemically conjugated chimeric molecule refers to any molecule that links/joins the constituent molecules of the chemically conjugated chimeric molecule.

"Antibody" refers to a polypeptide substantially encoded by at least one immunoglobulin gene or fragments of at least one immunoglobulin gene, that can participate in specific binding with a ligand. The term includes naturally-occurring forms, as well as fragments and derivatives. Fragments within the scope of the term as used herein include those produced by digestion with various peptidases, such as Fab, Fab' and F(ab)'2 fragments, those produced by chemical dissociation, by chemical cleavage, and recombinantly, so long as the fragment remains capable of specific binding to a target molecule, such as a host cell protein. Typical recombinant fragments, as are produced, e.g., by phage display, include single chain Fab and scFv ("single chain variable region") fragments. Derivatives within the scope of the term include antibodies (or fragments thereof) that have been modified in sequence, but remain capable of specific binding to a target molecule, including interspecies chimeric and humanized antibodies. As used herein, antibodies can be produced by any known technique, including harvest from cell culture of native B lymphocytes, hybridomas, recombinant expression systems, by phage display, or the like.

Accordingly, antibodies comprise a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

Accordingly, the term antibody also embraces minibodies, diabodies, triabodies and the like. Diabodies are small bivalent biospecific antibody fragments with high avidity and specificity. Their high signal to noise ratio is typically better due to a better specificity and fast blood clearance increasing their potential for diagnostic and therapeutic targeting of specific antigen (Sundaresan et al., *J Nucl Med* 44:1962-9 (2003). In addition, these antibodies are advantageous because they can be engineered if necessary as different types of antibody fragments ranging from a small single chain Fv to an intact IgG with varying isoforms (Wu & Senter, *Nat. Biotechnol.* 23:1137-1146 (2005)). In some embodiments, the antibody fragment is part of a diabody. Exemplary diabodies for use according to the invention include those designated herein as KS41, KS49, KS83, KS89.

For preparation of antibodies, e.g., recombinant, monoclonal, or polyclonal antibodies, many techniques known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* ($3^{rd}$ ed. 1997)). Techniques for the production of single chain antibodies or recombinant antibodies (U.S. Pat. No. 4,946, 778, U.S. Pat. No. 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332:323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Using Antibodies, A Laboratory Manual* (1998) for a description of immunoassay formats and conditions that can be used to determine specific immunoreactivity).

"Prognosis" refers to a forecast as to the probable outcome of a disease state a determination of the prospect as to recovery from a disease as indicated by the nature and symptoms of a case, the monitoring of the disease status of a patient, the monitoring of a patient for recurrence of disease, and/or the determination of the preferred therapeutic regimen for a patient.

"Quantification percentage" refers to a CAIX expression score that includes the percentage of a sample (e.g., a target tissue or cellular sample, such as a sample from a renal tumor, a sample from a metastatic lesion derived from a metastatic lesion, and/or the like) that has positive CAIX expression. In preferred embodiments, the quantification percentage of a sample refers a CAIX expression score that includes the extent of staining or staining percentage (e.g., the percentage of cells in a sample that stain positively for CAIX, etc.). In certain embodiments, other factors such as staining intensity and the percentage staining at maximal staining intensity are also included in a CAIX expression score for a particular sample. For example, as illustrated in an example provided below, survival tree analysis of CAIX scoring information from the analyzed tissue arrays identified that a staining percentage of 85% was an ideal cutoff for stratification for patient survival. Staining percentages >85%, irrespective of intensity, were considered high CAIX staining, whereas those ≤85% were considered low CAIX staining.

As noted above, we have identified a CAIX variant with novel cDNA and amino acidic sequences, using polymerase chain reaction (PCR) cloning methods and sequence analysis on samples from RCC patient tissues. The nucleic acid and protein sequence of the novel CAIX variant (alternatively referred to herein as the "mutant CAIX") differ from the CAIX sequences reported thus far (e.g., sequences in NCBI Gene/protein database and UniProtKB/Swiss-Prot protein database). In addition, fusion/chimeric molecules (GMCSF-CAIX) based on this newly identified CAIX variant have been constructed. The constructs are to be used, at least initially, for targeted kidney cancer vaccine therapy, based upon early laboratory results as well as the fact that GMCSF gene/vaccine therapy has been shown to have clinical anti-tumor activity in RCC.

Targeted Cancer Vaccine Therapy

As noted above, a CAIX variant with novel cDNA and amino acidic sequences from RCC patient tissues (and having entirely different sequences from those reported previously) is provided in the present invention. Among other advantages, the novel CAIX sequence can be used to generate more effective targeted vaccines for a variety of cancers that express CAIX on the cell surface.

For example, as a part of the research program of targeted kidney cancer vaccine therapy, a fusion/chimeric molecules (GMCSF-CAIX) based on the newly identified CAIX variant was constructed. The rationale for this approach is based on early laboratory results, as well as the fact that cytokine-gene/vaccine therapy has previously been shown to have anti-tumor activity in clinical trials. The novel human RCC CAIX variant was combined with GMCSF, a potent cytokine, to significantly enhance anti-cancer efficacy of CAIX-based vaccine.

The present invention provides fusion molecules of GMCSF-CAIXv, as well as GMCSF-CAIXv Adenoviral Vector Gene Delivery Systems. In a preferred embodiment, the pAd-CMV shuttle vector in current construction of GMCSF-CAIXv was utilized to replace GFP-containing padTrack-CMV shuttle vector reported previously in our laboratory. In addition, a nanotechnology platform combined with sustained/controlled delivery technology can be used to achieve longer-term expression of GMCSF-CAIXv fusion molecule, e.g., in dendritic cells.

Renal Cell Carcinoma Treatments

In view of the well-recognized importance of CAIX in RCC biology, the CAIX variant with novel cDNA/amino acidic sequences provided herein provides a new target for the development of new, specific strategies to augment anti-cancer efficacy, as well as for RCC disease progression and survival. Both the novel CAIXv protein and monoclonal antibodies directed thereto may be developed as therapeutics and diagnostics for CAIXv-expressing cancers. The novel CAIX variant can also be employed in strategies that target the signaling pathways regulated by CAIX.

Methods for Prognosis

The novel CAIX variant is also useful as a prognostic biomarker and pathway signature to evaluate the relative expression level of CAIX in cancerous tissue. For example, CAIX has been employed in the evaluation of RCC patients via collection of data from immunohistochemical analysis, RT-PCR and western blot, which were compared with measured expression levels in autologous normal kidney tissue, or with normal expression level of control tissue. The novel CAIX variant of the present invention provides an improved prognostic biomarker, and can be used in the methods described in U.S. Ser. No. 10/511,465 to Bui et al. and related PCT application PCT/US2003/11561, to provide prognostic information for patients afflicted with various CAIX-expressing cancers, in addition to renal cell carcinoma (RCC). The methods include quantifying CAIX. In addition to reliably predicting clinical outcome, the methods of the present invention also can be used to better identify high-risk patients in need of adjuvant immunotherapy and/or CAIX-targeted therapies, among other courses of treatment.

Chimeric Constructs

As noted above, the invention provides a novel approach to the treatment (e.g. mitigation of symptoms) of any type of cancer that expresses the novel CAIX variant or an antigen cross-reactive with CAIXv or CAIX (e.g. renal cell carcinoma, cervical cancer, bladder cancer, hypoxia-inducible cancers, and the like. In one embodiment of the invention, a chimeric molecule comprising the novel CAIX variant attached to a granulocyte-macrophage colony stimulating factor (GM-CSF) is provided. The chimeric molecule can be administered to a patient (e.g., by vaccination), leading to activation of antigen presenting cells (e.g., dendritic cells). Presentation of the CAIXv antigen on HLA class I then activates CAIX-specific cytotoxic T cells, which can then lyse CAIX-positive cancer cells. In addition, or alternatively, the CAIXv peptide is presented on HLA class II cells, resulting in activation of CAIX-specific T helper cells, which then activate or maintain the killing activity of CTLs.

Details with respect to the preparation and administration of chimeric constructs can be found, for example, in U.S. patent application Ser. No. 09/783,708 to Belldegrun et al., the contents of which are hereby incorporated by reference in their entirety.

This invention provides a novel approach to the treatment (e.g. mitigation of symptoms) of a renal cell carcinoma or any type of cancer that expresses CAIX, including particularly CAIXv. In particular this invention utilizes a chimeric molecule comprising a CAIXv attached to a granulocyte-macrophage colony stimulating factor (GM-CSF). In one embodiment, the GM-CSF has the sequence of SEQ ID NO:4. Without being bound to a particular theory, it is believed that this chimeric molecule affords two modes of activity. Vaccination of patients with advanced renal cell carcinoma using a chimeric CAIXv-GM-CSF molecule will result in activation of the patient's dendritic cells (DC), the most potent antigen presenting cells. The dendritic cells take up GM-CSF, e.g., via the GM-CSF receptor and the attached CAIXv is co-transported by virtue of its attachment to the GM-CSF. The dendritic cells process the CAIXvn and present CAIXv peptides on HLA class I which then activates CAIXv specific cytotoxic T cells (CD3$^+$CD8$^+$) which can then lyse CAIXv positive kidney cancer cells. In addition, or alternatively, the CAIXv peptide is presented on HLA class II cells that activate CAIXv specific T helper cells which then activate or maintain the killing activity of CTLs.

In certain embodiments, a nucleic acid encoding a CAIXv-GM-CSF construct can be administered as a "naked DNA" vaccine. In this approach, the organism/patient is injected, e.g. intramuscularly, with a nucleic acid encoding a CAIXv-GM-CSF fusion protein. The nucleic acid is expressed within the organism leading to the production of a CAIXv-GM-CSF fusion protein which then elicits an anti-renal cell carcinoma immune response as described above.

In another embodiment, the chimeric CAIXv-GM-CSF molecules can be used in adoptive immunotherapy. In this instance, the chimeric molecule (fusion protein) or a nucleic acid encoding the chimeric molecule is used to activate lymphocytes (e.g. T-cells) ex vivo. The activated lymphocytes are optionally expanded, ex vivo, and then re-infused back into the subject (patient) where they specifically attack and lyse CAIXv positive tumor cells (e.g. kidney cells tumor or cervical cancer cells).

In particularly preferred embodiments, this invention utilizes one or more of the following formulations:

1. A polypeptide comprising a fusion protein of GM-CSF (e.g., a GM-CSF polypeptide of SEQ ID NO:4) and a CAIXv polypeptide.
2. Dendritic, or other cells, pulsed with a polypeptide comprising GM-CSF and CAIXv as a fusion protein;
3. Nucleic acids encoding a fusion protein of GM-CSF and CAIXv in a "gene therapy" vector (e.g. adenovirus, gutless-adenovirus, retrovirus, lantivirus, adeno-associated virus, vaccinia virus, simian virus 40, etc.)
4. Dendritic cells transfected with a nucleic acid encoding a fusion protein of GM-CSF and CAIXv (e.g., via recombinant virus, plasmid DNA transfection, and the like);
5. Tumor cells (e.g. RCC cells) comprising a nucleic acid encoding a fusion protein of GM-CSF and CAIXv;
6. A nucleic acid encoding a fusion protein of GM-CSF and CAIXv (e.g. "naked DNA"); and
7. A nucleic acid encoding a fusion protein of GM-CSF and CAIXv complexed with a transfection agent (e.g., DMRIE/DOPE lipid, dendrimers, etc.).

Each of these formulations can be directly administered to an organism (e.g. a mammal having a cancer that expresses CAIXv, or an antigen cross-reactive to a CAIXv antigen) or can be used in an adoptive immunotherapy context. In the latter approach, the adoptive immunotherapy preferably utilizes cells derived from peripheral blood (e.g. peripheral blood lymphocytes (PBLs) or cells derived from a tumor (e.g. tumor infiltrating lymphocytes (TILs)). Administration of the formulation results in activation and propagation of CAIXv-targeted cytotoxic T cells in PBMC or TIL cultures. Infusion of the CAIXv-targeted CTLs into the patient results in the development and maintenance of a CAIXv-directed immune response.

The formulations identified above can also be administered directly to a mammal for "in vivo" vaccination. Thus, for example, GM-CSF-CAIXv polypeptides or nucleic acids encoding such polypeptides can be administered to the organism as "traditional" vaccines. The other immunogenic formulations identified above, however, are also highly active in vivo and can also be "directly" administered to an organism as a "vaccine". Thus, for example, dendritic cells pulsed with a GM-CSF-CAIXv fusion protein, dendritic, or other cells, transfected with a nucleic acid encoding a GM-CSF-CAIXv fusion protein, gene therapy vectors encoding a GM-CSF-CAIXv polypeptide, can all be administered to an organism where they induce and maintain a population of CAIXv-directed cytotoxic T cells.

CAIXv-GM-CSF chimeric molecules e.g. when used in vivo as a vaccine or in an adoptive immunotherapeutic modality can induce a highly vigorous immune response specifically directed at renal cell carcinomas. The approach results in the death or inhibition of neoplastic renal cells whether diffuse (e.g. motile metastatic cells) or aggregated (e.g. as in a solid tumor). These methods can accompany administration of other agents (e.g. immunomodulatory or cytotoxic agents, such as cytokines or drugs).

It is recognized that the methods of this invention need not show complete tumor elimination (e.g. a "cure") to be of value. Even a slight decrease in the growth rate of a tumor, and/or in the propagation of metastatic, or other neoplastic, cells can be clinically relevant improving the quality and/or duration of life. Of course, given the high efficacy observed, it is expected that the methods of this invention may offer a significant or complete degree of remission particularly when used in combination with other treatment modalities (e.g. surgery, chemotherapy, interleukin therapy, TGFβ or IL-10 antisense therapy, etc.).

I. CAIXv-GMCSF Chimeric Molecules and their Expression

This invention utilizes a chimeric molecule comprising a CAIXv kidney cancer-specific antigen attached to a granulocyte-macrophage colony stimulating factor (GM-CSF/GMCSF). to induce a cell-mediated immune response targeted to renal tumor cells. In a chimeric molecule, two or more molecules that exist separately in their native state are joined together to form a single molecule having the desired functionality of all of its constituent molecules. In this instance, the constituent molecules are CAIXv and GM-CSF respectively. The CAIXv provides an epitope that is presented (e.g. to T-cells) resulting in activation and expansion of those cells and the formation of cytotoxic cells (e.g. cytotoxic T lymphocytes, tumor infiltrating lymphocytes (TILs), etc.) that are direct to tumor cells bearing the CAIXv or a CAIXv antigen. The GM-CSF acts both to stimulate components of the immune system (e.g. monocytes, dendritic cells, NK, PMN, PBMC, etc.) and to mediate uptake of the associated CAIXv or CAIXv antigen by dendritic cells. In addition, particularly in adoptive immunotherapeutic modalities, the GM-CSF also can act as an adjuvant.

The attachment of the CAIXv to the GM-CSF can be direct (e.g. a covalent bond) or indirect (e.g. through a linker). In addition, the CAIXv and the GM-CSF proteins can be attached by chemical modification of the proteins or they can be expressed as a recombinant fusion protein. Detailed methods of producing the individual components and the chimeric molecule are provided below.

The nucleic acid sequence of CAIXv is disclosed herein. The nucleic acid sequence of GM-CSF (e.g. human GM-CSF) is well known to those of skill in the art (see, e.g., GenBank accession no: E02287).

Using this sequence information nucleic acids encoding CAIXv, GM-CSF, or a chimeric CAIXv-GM-CSF can be produced using standard methods well known to those of skill in the art. For example, the nucleic acid(s) may be cloned, or amplified by in vitro methods, such as the polymerase chain reaction (PCR), the ligase chain reaction (LCR), the transcription-based amplification system (TAS), the self-sustained sequence replication system (SSR), etc. A wide variety of cloning and in vitro amplification methodologies are well known to persons of skill in the art.

Examples of these techniques and instructions sufficient to direct persons of skill through many cloning exercises are found in Berger and Kimmel, Guide to Molecular Cloning Techniques, Methods in Enzymology 152 Academic Press, Inc., San Diego, Calif. (Berger); Sambrook et al. (1989) Molecular Cloning—A Laboratory Manual (2nd ed.) Vol. 1-3, Cold Spring Harbor Laboratory, Cold Spring Harbor Press, NY, (Sambrook et al.); Current Protocols in Molecular Biology, F. M. Ausubel et al., eds., Current Protocols, a joint venture between Greene Publishing Associates, Inc. and John Wiley & Sons, Inc., (1994 Supplement) (Ausubel); Cashion et al., U.S. Pat. No. 5,017,478; and Carr, European Patent No. 0,246,864.

Examples of techniques sufficient to direct persons of skill through in vitro amplification methods are found in Berger, Sambrook, and Ausubel, as well as Mullis et al., (1987) U.S. Pat. No. 4,683,202; PCR Protocols A Guide to Methods and Applications (Innis et al. eds) Academic Press Inc. San Diego, Calif. (1990) (Innis); Arnheim & Levinson (Oct. 1, 1990) C&EN 36-47; The Journal Of NIH Research (1991) 3: 81-94; (Kwoh et al. (1989) Proc. Natl. Acad. Sci. USA 86: 1173; Guatelli et al. (1990) Proc. Natl. Acad. Sci. USA 87, 1874; Lomeli et al. (1989) J. Clin. Chem., 35: 1826; Landegren et al., (1988) Science, 241: 1077-1080; Van Brunt (1990) Biotechnology, 8: 291-294; Wu and Wallace, (1989) Gene, 4: 560; and Barringer et al. (1990) Gene, 89: 117.

The CAIXv and the GM-CSF molecules of a CAIXv-GMCSF construct may be joined together in any order. Thus, the CAIXv can be joined to either the amino or carboxy termini of the GM-CSF. Where the molecules are chemically conjugated, they need not be joined end to end and can be attached at any convenient terminal or internal site.

The CAIXv and GM-CSF may be attached by any of a number of means well known to those of skill in the art. Typically the CAIXv and the GM-CSF are conjugated, either directly or through a linker (spacer). Because both molecules are polypeptides, in one embodiment, it is preferable to recombinantly express the chimeric molecule as a single-chain fusion protein that optionally contains a peptide spacer between the GM-CSF and the CAIXv.

Means of chemically conjugating molecules are well known to those of skill. Polypeptides typically contain variety of functional groups; e.g., carboxylic acid (COOH) or free amine ($-NH_2$) groups, which are available for reaction with a suitable functional group on an effector molecule to bind the effector thereto.

A "linker", as used herein, is a molecule that is used to join the CAIXv to the GM-CSF. In preferred embodiments, the linker is capable of forming covalent bonds to both the CAIXv and GM-CSF. Suitable linkers are well known to those of skill in the art and include, but are not limited to, straight or branched-chain carbon linkers, heterocyclic carbon linkers, or peptide linkers. In certain embodiments, the linkers may be joined to amino acids comprising CAIXv and/or GM-CSF through their side groups (e.g., through a disulfide linkage to cysteine). However, in a preferred embodiment, the linkers will be joined to the alpha carbon amino and carboxyl groups of the terminal amino acids. The linker may be bifunctional, having one functional group reactive with a substituent on the CAIXv and a different functional group reactive with a substituent on the GM-CSF. Alternatively, the CAIXv and/or the GM-CSF may be derivatized to react with a "mono-functional" linker (see, e.g., U.S. Pat. Nos. 4,671,958 and 4,659,839 for procedures to generate reactive groups on peptides).

In a particularly preferred embodiment, the chimeric molecules of this invention are fusion proteins. The fusion protein can be chemically synthesized using standard chemical peptide synthesis techniques, or, more preferably, recombinantly expressed. Where both molecules are relatively short the chimeric molecule may be synthesized as a single contiguous polypeptide. Solid phase synthesis in which the C-terminal amino acid of the sequence is attached to an insoluble support followed by sequential addition of the remaining amino acids in the sequence is a preferred method for the chemical synthesis of the polypeptides of this invention. Techniques for solid phase synthesis are described by Barany and Merrifield, Solid-Phase Peptide Synthesis; pp. 3-284 in The Peptides: Analysis, Synthesis, Biology. Vol. 2: Special Methods in Peptide Synthesis, Part A., Merrifield, et al. J. Am. Chem. Soc., 85: 2149-2156 (1963), and Stewart et al., Solid Phase Peptide Synthesis, 2nd ed. Pierce Chem. Co., Rockford, Ill. (1984).

In a most preferred embodiment, the chimeric fusion proteins of the present invention are synthesized using recombinant DNA methodology. Generally this involves creating a DNA sequence that encodes the fusion protein, placing the DNA in an expression cassette under the control of a particular promoter, expressing the protein in a host, isolating the expressed protein and, if required, renaturing the protein.

In one embodiment, accordingly, the invention provides a nucleic acid which encodes a fusion of hGMCSF with hCAIXv of the sequence (SEQ ID NO:7):

```
(hGMCSF)-(linker)-(CAIXv):
ATGTGGCTGCAGAGCCTGCTGCTCTTGGGCACTGTGGCCTGCAGCATCT

CTGCACCCGCCCGCTCGCCCAGCCCCAGCACGCAGCCCTGGGAGCATGT

GAATGCCATCCAGGAGGCCCGGCGTCTCCTGAACCTGAGTAGAGACACT

GCTGCTGAGATGAATGAAACAGTAGAAGTCATCTCAGAAATGTTTGACC

TCCAGGAGCCGACCTGCCTACAGACCCGCCTGGAGCTGTACAAGCAGGG

CCTGCGGGGCAGCCTCACCAAGCTCAAGGGCCCCTTGACCATGATGGCC

AGCCACTACAAGCAGCACTGCCCTCCAACCCCGGAAACTTCCTGTGCAA

CCCAGACTATCACCTTTGAAAGTTTCAAAGAGAACCTGAAGGACTTTCT

GCTTGTCATCCCCTTTGACTGCTGGGAGCCAGTCCAGGAG

AAGCTT

ATGGCTCCCCTGTGCCCCAGCCCCTGGCTCCCTCTGTTGATCCCGGCCC

CTGCTCCAGGCCTCACTGTGCAACTGCTGCTGTCACTGCTGCTTCTGAT

GCCTGTCCATCCCCAGAGGTTGCCCCGGATGCAGGAGGATTCCCCCTTG

GGAGGAGGCTCTTCTGGGGAAGATGACCCACTGGGCGAGGAGGATCTGC

CCAGTGAAGAGGATTCGCCCAGAGAGGAGGATCCACCCGGAGAGGAGGA

TCTACCTGGAGAGGAGGATCTACCTGGAGAGGAGGATCTACCTGAAGTT

AAGCCTAAATCAGAAGAAGAGGGCTCCCTGAAGTTAGAGGATCTACCTA

CCGTTGAGGCTCCTGGAGGTCCTCAAGAACCCCAGAATAATGCCCACAG

GGACAAAGAAGGGGATGACCAGAGTCATTGGCGCTATGGAGGCGACCCG

CCCTGGCCCCGGGTGTCCCCAGCCTGCGCGGGCCGCTTCCAGTCCCCGG

TGGATATCCGCCCCCAGCTCGCCGCCTTCTGCCCGGCCCTGCGCCCCCT

GGAACTCCTGGGCTTCCAGCTCCCGCCGCTCCCAGAACTGCGCCTGCGC

AACAATGGCCACAGTGTGCAACTGACCCTGCCTCCTGGGCTAGAGATGG
```

```
CTCTGGGTCCCGGGCGGGAGTACCGGGCTCTGCAGCTGCATCTGCACTG

GGGGGCTGCAGGTCGTCCGGGCTCGGAGCACACTGTGGAAGGCCACCGT

TTCCCTGCCGAGATCCACGTGGTTCACCTCAGCACCGCCTTTGCCAGAG

TTGACGAGGCCTTGGGGCGCCCGGGAGGCCTGGCCGTGTTGGCCGCCTT

TCTGGAGGAGGGCCCGGAAGAAAACAGTGCCTATGAGCAGTTGCTGTCT

CGCTTGGAAGAAATCGCTGAGGAAGGCTCAGAGACTCAGGTCCCAGGAC

TGGACATATCTGCACTCCTGCCCTCTGACTTCAGCCGCTACTTCCAATA

TGAGGGGTCTCTGACTACACCGCCCTGTGCCCAGGGTGTCATCTGGACT

GTGTTTAACCAGACAGTAATGCTGAGTGCTAAGCAGCTCCACACCCTCT

CTGACACCCTGTGGGGACCCGGTGACTCTCGGCTACAACTGAGCTTCCG

AGCGACGCAGCCTTTGAATGGGCGAGTGATTGAGGCCTCCTTCCCTGCT

GGAGTGGACAGCAGTCCTCGGGCTGCTGAGCCAGTCCAGCTGAATTCCT

GCCTGGCTGCTGGTGACATTCTAGCCCTGGTTTTTGGCCTCCTTTTTGC

TGTCACCAGCGTCGCGTTCCTTGTGCAGATGAGAAGGCAGCACAGAAGG

GGAACCAAAGGGGGTGTGAGCTACCGCCCAGCAGAGGTAGCCGAGACTG

GAGCCTAG
```

In another embodiment, the invention provides a nucleic acid sequence encoding a fusion protein (SEQ ID NO:8) of the human GMCSF protein sequence and the CAIXv protein sequence joined by a polypeptide linker (e.g., -Lys-Leu-).

```
hGMCSF
MWLQSLLLLGTVACSISAPARSPSPSTQPWEHVNAIQEARRLLNLSR

DTAAEMNETVEVISEMFDLQEPTCLQTRLELYKQGLRGSLTKLKGPL

TMMASHYKQHCPPTPETSCATQTITFESFKENLKDFLLVIPFDCWEP

VQE linker (e.g., -Lys-Leu-)

CAIXv protein
MAPLCPSPWLPLLIPAPAPGLTVQLLLSLLLLMPVHPQRLPRMQEDS

PLGGGSSGEDDPLGEEDLPSEEDSPREEDPPGEEDLPGEEDLPGEEDL

PEVKPKSEEEGSLKLEDLPTVEAPGGPQEPQNNAHRDKEGDDQSHW

RYGGDPPWPRVSPACAGRFQSPVDIRPQLAAFCPALRPLELLGFQLP

PLPELRLRNNGHSVQLTLPPGLEMALGPGREYRALQLHLHWGAAGR

PGSEHTVEGHRFPAEIHVVHLSTAFARVDEALGRPGGLAVLAAFLEE

GPEENSAYEQLLSRLEEIAEEGSETQVPGLDISALLPSDFSRYFQYEG

SLTTPPCAQGVIWTVFNQTVMLSAKQLHTLSDTLWGPGDSRLQLSFR

ATQPLNGRVIEASFPAGVDSSPRAAEPVQLNSCLAAGDILALVFGLLF

AVTSVAFLVQMRRQHRRGTKGGVSYRPAEVAETGA
```

DNA encoding the fusion protein of this invention (GM-CSF-CAIXv) may be prepared by any suitable method, including, for example, cloning and restriction of appropriate sequences or direct chemical synthesis by methods such as the phosphotriester method of Narang et al Meth. Enzymol. 68: 90-99 (1979); the phosphodiester method of Brown et al., Meth. Enzymol. 68: 109-151 (1979); the diethylphosphoramidite method of Beaucage et al., Tetra. Lett., 22: 1859-1862 (1981); and the solid support method of U.S. Pat. No. 4,458,066.

Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

Alternatively, subsequences may be cloned and the appropriate subsequences cleaved using appropriate restriction enzymes. The fragments may then be ligated to produce the desired DNA sequence.

In a preferred embodiment, DNA encoding fusion proteins of the present invention is using DNA amplification methods such as polymerase chain reaction (PCR).

The nucleic acid constructs can have a linker (gcggcg) between the nucleic acids encoding CAIXv and GM-CSF. The linker sequence is used to separate GM-CSF and CAIXv by a distance sufficient to ensure that, in a preferred embodiment, each domain properly folds into its secondary and tertiary structures. Preferred peptide linker sequences adopt a flexible extended conformation, do not exhibit a propensity for developing an ordered secondary structure that could interact with the functional GM-CSF and CAIXv domains. Typical amino acids in flexible protein regions include Gly, Asn and Ser. Virtually any permutation of amino acid sequences containing Gly, Asn and Ser would be expected to satisfy the above criteria for a linker sequence. Other near neutral amino acids, such as Thr and Ala, also may be used in the linker sequence. Thus, amino acid sequences useful as linkers of GM-CSF and CAIXv include the $Gly_4SerGly_5Ser$ linker (SEQ ID NO:5) used in U.S. Pat. No. 5,108,910 or a series of four (Ala Gly Ser) residues (SEQ ID NO:6), etc. Still other amino acid sequences that may be used as linkers are disclosed in Maratea et al. (1985), Gene 40: 39-46; Murphy et al. (1986) Proc. Nat'l. Acad. Sci. USA 83: 8258-62; U.S. Pat. No. 4,935,233; and U.S. Pat. No. 4,751,180.

The length of the peptide linker sequence may vary without significantly affecting the biological activity of the fusion protein. In one preferred embodiment of the present invention, a peptide linker sequence length of about 2 amino acids is used to provide a suitable separation of functional protein domains, although longer linker sequences also may be used. The linker sequence may be from 1 to 50 amino acids in length. In the most preferred aspects of the present invention, the linker sequence is from about 1-20 amino acids in length. In the specific embodiments disclosed herein, the linker sequence is from about 2 to about 15 amino acids, and is advantageously from about 2 to about 10 amino acids. Peptide linker sequences not necessarily required in the fusion proteins of this invention.

Generally the spacer will have no specific biological activity other than to join the proteins or to preserve some minimum distance or other spatial relationship between them. However, the constituent amino acids of the spacer may be selected to influence some property of the molecule such as the folding, net charge, or hydrophobicity.

Where it is desired to recombinantly express either the CAIXv, the GM-CSF, or the CAIXv-GM-CSF fusion protein, the nucleic acid sequences encoding the desired protein are typically operably linked to suitable transcriptional or translational regulatory elements. The regulatory elements typically include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants may additionally be incorporated.

The nucleic acid sequences encoding the fusion proteins may be expressed in a variety of host cells, including *E. coli* and other bacterial hosts, and eukaryotic host cells including but not limited to yeast, insect cells (e.g. SF9 cells) and various other eukaryotic cells such as the COS, CHO and HeLa cells lines and myeloma cell lines. The recombinant protein gene will be operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences. In one particularly preferred embodiment the GM-CSF-CAIXv fusion gene is inserted into polyhedrin gene locus-based baculovirus transfer vector (e.g., pVL 1393, available from PharMingen) and expressed in insect cells (e.g. SF9 cells).

In view of the redundancy of the genetic code, in any of the embodiments using a nucleic acid according to the invention, the sequence of the nucleic acid encoding the protein can optionally be optimized for expression in bacteria, human cells, mammalian cells, insect cells or in vitro translation as known to one of ordinary skill in the art.

The plasmids of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo, and hyg genes.

Once expressed, the recombinant fusion proteins can be purified according to standard procedures of the art, including ammonium sulfate precipitation, his tag capture, affinity columns, column chromatography, gel electrophoresis and the like (see, generally, R. Scopes, Protein Purification, Springer-Verlag, N.Y. (1982), Deutscher, Methods in Enzymology Vol. 182: Guide to Protein Purification., Academic Press, Inc. N.Y. (1990)). Substantially pure compositions of at least about 90 to 95% homogeneity are preferred, and 98 to 99% or more homogeneity are most preferred for pharmaceutical uses. Once purified, partially or to homogeneity as desired, the polypeptides may then be used therapeutically.

One of skill in the art would recognize that after chemical synthesis, biological expression, or purification, the CAIXv, GM-CSF, or GM-CSF-CAIXv protein may possess a conformation substantially different than the native conformations of the polypeptide(s). In this case, it may be necessary to denature and reduce the polypeptide and then to cause the polypeptide to re-fold into the preferred conformation. Methods of reducing and denaturing proteins and inducing re-folding are well known to those of skill in the art (See, Debinski et al. (1993) J. Biol. Chem., 268: 14065-14070; Kreitman and Pastan, (1993) Bioconjug. Chem., 4: 581-585; and Buchner, et al., (1992) Anal. Biochem., 205: 263-270).

Debinski et al., for example, describe the denaturation and reduction of inclusion body proteins in guanidine-DTE. The protein is then refolded in a redox buffer containing oxidized glutathione and L-arginine.

One of skill would recognize that modifications can be made to the GM-CSF, CAIXv, or GM-CSF-CAIXv proteins without diminishing their biological activity. Some modifications may be made to facilitate the cloning, expression, or incorporation of the constituent molecules into a fusion protein. Such modifications are well known to those of skill in the art and include, for example, a methionine added at the amino terminus to provide an initiation site, or additional amino acids placed on either terminus to create conveniently located restriction sites or termination codons, or to simplify purification such as polyhistidine tag sequence.

II. In Vivo Protein Vaccination

Immunogenic compositions (e.g. vaccines) are preferably prepared from the CAIXv-GM-CSF fusion proteins of this invention. The immunogenic compositions including vaccines may be prepared as injectables, as liquid solutions, suspensions or emulsions. The active immunogenic ingredient or ingredients may be mixed with pharmaceutically acceptable excipients which are compatible therewith. Such excipients are well known to those of skill in the art and include, but are not limited to water, saline, dextrose, glycerol, ethanol, and combinations thereof. The immunogenic compositions and vaccines may further contain auxiliary substances, such as wetting or emulsifying agents, pH buffering agents, or adjuvants to enhance the effectiveness thereof.

The immunogenic CAIXv-GM-CSF compositions may be administered parenterally, by injection subcutaneous, intravenous, intradermal, intratumoral, or intramuscularly injection. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories and oral formulations may be desirable. For suppositories, binders and carriers may include, for example, polyalkalene glycols or triglycerides. Such suppositories may be formed from mixtures containing the active immunogenic ingredient (s) in the range of about 0.5 to about 10%, preferably about 1 to 2%. Oral formulations may include normally employed carriers such as, pharmaceutical grades of saccharine, cellulose and magnesium carbonate. These compositions can take the form of solutions, suspensions, tablets, pills, capsules, sustained release formulations or powders and contain about 1 to 95% of the active ingredient(s), preferably about 20 to about 75%.

The immunogenic preparations and vaccines are administered in a manner compatible with the dosage formulation, and in such amount as will be therapeutically effective, immunogenic and protective. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art and may be of the order of micrograms to milligrams of the active ingredient(s) per vaccination. The antigenic preparations of this invention can be administered by either single or multiple dosages of an effective amount. Effective amounts of the compositions of the invention can vary from 0.01-1,000 microgram/ml per dose, more preferably 0.1-500 microgram/ml per dose, and most preferably 10-300 microgram/ml per dose.

Suitable regimes for initial administration and booster doses are also variable, but may include an initial administration followed by subsequent booster administrations. The dosage may also depend or the route of administration and will vary according to the size of the host.

The concentration of the active ingredient (chimeric protein) in an immunogenic composition according to the invention is in general about 1 to 95%.

Immunogenicity can be significantly improved if the antigens are co-administered with adjuvants. While the GM-CSF component of the chimeric molecule can, itself act as an adjuvant, other adjuvants can be used as well. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Intrinsic adjuvants, such as lipopolysaccharides, normally are the components of the killed or attenuated bacteria used as vaccines. Extrinsic adjuvants are immunomodulators which are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established and a HBsAg vaccine has been adjuvanted with alum.

A wide range of extrinsic adjuvants can provoke potent immune responses to antigens. These include saponins complexed to membrane protein antigens (immune stimulating complexes), pluronic polymers with mineral oil, killed mycobacteria in mineral oil, Freund's incomplete adjuvant, bacterial products, such as muramyl dipeptide (MDP) and lipopolysaccharide (LPS), as well as lipid A, and liposomes.

To efficiently induce humoral immune responses (HIR) and cell-mediated immunity (CMI), immunogens are often emulsified in adjuvants. Many adjuvants are toxic, inducing granulomas, acute and chronic inflammations (Freund's complete adjuvant, FCA), cytolysis (saponins and Pluronic polymers) and pyrogenicity, arthritis and anterior uveitis (LPS and MDP). Although FCA is an excellent adjuvant and widely used in research, it is not licensed for use in human or veterinary vaccines because of its toxicity.

III. In Vivo DNA Vaccination

In some preferred embodiments, nucleic acids encoding a CAIXv-GM-CSF fusion protein are incorporated into DNA vaccines. The ability of directly injected DNA, that encodes an antigenic protein, to elicit a protective immune response has been demonstrated in numerous experimental systems (see, e.g., Conry et al. (1994) Cancer Res., 54: 1164-1168; Cox et al. (1993) Virol, 67: 5664-5667; Davis et al. (1993) Hum. Mole. Genet., 2: 1847-1851; Sedegah et al. (1994) Proc. Natl. Acad. Sci., USA, 91: 9866-9870; Montgomery et al. (1993) DNA Cell Bio., 12: 777-783; Ulmer et al. (1993)

Science, 259: 1745-1749; Wang et al. (1993) Proc. Natl. Acad. Sci., USA, 90: 4156-4160; Xiang et al. (1994) Virology, 199: 132-140, etc.).

Vaccination through directly injecting DNA, that encodes an antigenic protein, to elicit a protective immune response often produces both cell-mediated and humoral responses. Moreover, reproducible immune responses to DNA encoding various antigens have been reported in mice that last essentially for the lifetime of the animal (see, e.g., Yankauckas et al. (1993) DNA Cell Biol., 12: 771-776).

As indicated above, DNA vaccines are known to those of skill in the art (see, also U.S. Pat. Nos. 5,589,466 and 5,593,971, PCT/US90/01515, PCT/US93/02338, PCT/US93/048131, PCT/US94/00899, and the priority applications cited therein. In addition to the delivery protocols described in those applications, alternative methods of delivering DNA are described in U.S. Pat. Nos. 4,945,050 and 5,036,006.

Using DNA vaccine technology, plasmid (or other vector) DNA that includes a sequence encoding a CAIXv-GM-CSF fusion protein operably linked to regulatory elements required for gene expression is administered to individuals (e.g. human patients, non-human mammals, etc.). The cells of the individual take up the administered DNA and the coding sequence is expressed. The antigen so produced becomes a target against which an immune response is directed. In the present case, the immune response directed against the antigen component of the chimeric molecule provides the prophylactic or therapeutic benefit to the individual renal cell cancers.

The vaccines of this invention may be administered by a variety of techniques including several different devices for administering substances to tissue. The published literature includes several review articles that describe aspects of DNA vaccine technology and cite some of the many reports of results obtained using the technology (see, e.g., McDonnel and Askari (1996) New Engl. J. Med. 334(1): 42-45; Robinson (1995) Can. Med. Assoc. J. 152(10): 1629-1632; Fynan et al. (1995) Int. J Immunopharmac. 17(2): 79-83; Pardoll and Beckerleg (1995) Immunity 3: 165-169; and Spooner et al. (1995) Gene Therapy 2: 173-180.

According to the present invention, the CAIXv-GM-CSF coding sequence is inserted into a plasmid (or other vector) which is then used in a vaccine composition. In preferred embodiments, the CAIXv-GM-CSF coding sequence is operably linked to regulatory elements required for expression of the construct in eukaryotic cells. Regulatory elements for DNA expression include, but are not limited to a promoter and a polyadenylation signal. In addition, other elements, such as a Kozak region, may also be included in the genetic construct. Initiation and termination signals are regulatory elements which are often, but not necessarily, considered part of the coding sequence. In preferred embodiments, the coding sequences of genetic constructs of this invention include functional initiation and termination signals.

Examples of promoters useful to practice the present invention, especially in the production of a genetic vaccine for humans, include but are not limited to, promoters from Simian Virus 40 (SV40), Mouse Mammary Tumor Virus (MMTV) promoter, Human Immunodeficiency Virus (HIV) such as the HIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV) as well as promoters from human genes such as human Actin, human Myosin, human Hemoglobin, human muscle creatine and human metallothionein.

Examples of polyadenylation signals useful to practice the present invention, especially in the production of a genetic vaccine for humans, include but are not limited to SV40 polyadenylation signals and LTR polyadenylation signals. In particular, the SV40 polyadenylation signal which is in pCEP4 plasmid (Invitrogen, San Diego, Calif.), referred to as the SV40 polyadenylation signal, may be used.

In addition to the regulatory elements required for DNA expression, other elements may also be included in the DNA molecule. Such additional elements include enhancers. The enhancer may be selected from the group including but not limited to, human Actin, human Myosin, human Hemoglobin, human muscle creatine and viral enhancers such as those from CMV, RSV and EBV.

The present invention relates to methods of introducing genetic material into the cells of an individual in order to induce immune responses against renal cell cancers. The methods comprise the steps of administering to the tissue of said individual, DNA that includes a coding sequence for a CAIXv-GM-CSF fusion protein operably linked to regulatory elements required for expression. The DNA can be administered in the presence of adjuvants or other substances that have the capability of promoting DNA uptake or recruiting immune system cells to the site of the inoculation. It should be understood that, in preferred embodiments, the DNA transcription unit itself is expressed in the host cell by transcription factors provided by the host cell, or provided by a DNA transcriptional unit. A DNA transcription unit can comprise nucleic acids that encode proteins that serve to stimulate the immune response such as a cytokine, proteins that serve as an adjuvant and proteins that act as a receptor.

Vectors containing the nucleic acid-based vaccine of the invention can be introduced into the desired host by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al (1992) J. Biol. Chem. 267: 963-967; Wu and Wu (1988) J. Biol. Chem. 263: 14621-14624). The subject can be inoculated intramuscularly, intranasally, intraperitoneally, subcutaneously, intradermally, topically, or by a gene gun.

The subject can also be inoculated by a mucosal route. The DNA transcription unit can be administered to a mucosal surface by a variety of methods, including lavage, DNA-containing nose-drops, inhalants, suppositories or by microsphere encapsulated DNA. For example, the DNA transcription unit can be administered to a respiratory mucosal surface, such as the trachea or into any surface including the tongue or mucous membrane.

The DNA transcription units are preferably administered in a medium, i.e., an adjuvant, that acts to promote DNA uptake and expression. Preferably, a pharmaceutically acceptable, inert medium is suitable as an adjuvant for introducing the DNA transcription unit into the subject. One example of a suitable adjuvant is alum (alumina gel), though even a saline solution is acceptable. Other possible adjuvants include organic molecules such as squalines, iscoms, organic oils and fats.

An immuno-effector can be co-expressed with the CAIXv-GM-CSF nucleic acid of this present invention and thereby enhance the immune response to the antigen. A nucleic acid encoding the immuno-effector may be administered in a separate DNA transcription unit, operatively linked to a suitable DNA promoter, or alternatively the immuno-effector may be included in a DNA transcription unit comprising a nucleic acid that encodes the CAIXv-GM-CSF construct that are operatively linked to one or more DNA promoters. Other embodiments contain two or more such immuno-effectors operatively linked to one or more promoters. The nucleic acid can consist of one contiguous polymer, encoding both the chimeric protein and the immuno-effector or it can consist of independent nucleic acid segments that individually encode the chimeric molecule and the immuno-effector respectively. In the latter case, the nucleic acid may be inserted into one vector or the independent nucleic acid segments can be placed into separate vectors. The nucleic acid encoding the immuno-effector and the chimeric molecule may be either operatively linked to the same DNA promoter or operatively linked to separate DNA promoters. Adding such an immuno-effector is known in the art. Alternatively, soluble immuno-effector proteins (cytokines, monokines, interferons, etc.) can be directly administered into the subject in conjunction with the CAIXv-GM-CSF DNA.

Examples of immuno-effectors include, but are not limited to, interferon-α, interferon-γ, interferon-β, interferon-T, interferon-θ, tumor necrosis factor-α, tumor necrosis factor-β, interleukin-2, interleukin-6, interleukin-7, interleukin-12, interleukin-15, B7-1 T cell co-stimulatory molecule, B7-2 T cell co-stimulatory molecule, immune cell adhesion molecule (ICAM)-1, T cell co-stimulatory molecule, granulocyte colony stimulatory factor, granulocyte-macrophage colony stimulatory factor, and combinations thereof.

When taken up by a cell, the genetic construct(s) may remain present in the cell as a functioning extrachromosomal molecule and/or integrate into the cell's chromosomal DNA. DNA may be introduced into cells where it remains as separate genetic material, e.g., in the form of a plasmid or plasmids. Alternatively, linear DNA which can integrate into the chromosome may be introduced into the cell. When introducing DNA into the cell, reagents which promote DNA integration into chromosomes may be added. DNA sequences which are useful to promote integration may also be included in the DNA molecule. Alternatively, RNA may be administered to the cell. It is also contemplated to provide the genetic construct as a linear minichromosome including a centromere, telomeres and an origin of replication. Gene constructs may remain part of the genetic material in attenuated live microorganisms or recombinant microbial vectors which live in cells. Gene constructs may be part of genomes of recombinant viral vaccines where the genetic material either integrates into the chromosome of the cell or remains extrachromosomal.

Genetic constructs can be provided with a mammalian origin of replication in order to maintain the construct extrachromosomally and produce multiple copies of the construct in the cell. Thus, for example, plasmids pCEP4 and pREP4 from Invitrogen (San Diego, Calif.) contain the Epstein Barr virus origin of replication and nuclear antigen EBNA-1 coding region which produces high copy episomal replication without integration.

An additional element may be added which serves as a target for cell destruction if it is desirable to eliminate cells receiving the genetic construct for any reason. A herpes thymidine kinase (tk) gene in an expressible form can be included in the genetic construct. The drug gangcyclovir can be administered to the individual and that drug will cause the selective killing of any cell producing tk, thus, providing the means for the selective destruction of cells with the CAIXv-GM-CSF nucleic acid construct.

In order to maximize protein production, regulatory sequences may be selected which are well suited for gene expression in the cells into which the construct is administered. Moreover, codons may be selected which are most efficiently transcribed in the cell. One having ordinary skill in the art can produce DNA constructs which are functional in the cells.

The concentration of the dosage is preferably sufficient to provide an effective immune response. The dosage of the recombinant vectors administered will depend upon the properties of the formulation employed, e.g., its in vivo plasma half-life, the concentration of the recombinant vectors in the formulation, the administration route, the site and rate of dosage, the clinical tolerance of the subject, and the like, as is well within the skill of one skilled in the art. Different dosages may be utilized in a series of inoculations; the practitioner may administer an initial inoculation and then boost with relatively smaller doses of the recombinant vectors or other boosters.

The preferred dose range is between about 30 microgram to about 1 mg DNA, and more preferably between about 50 microgram to 500 microgram. Lower doses may be used as plasmid expression and inoculation are optimized. Dosages may differ for adults in contrast to adolescents or children. The inoculation is preferably followed by boosters.

IV. Adoptive Immunotherapy

Adoptive immunotherapy refers to a therapeutic approach for treating cancer or infectious diseases in which immune cells are administered to a host with the aim that the cells mediate either directly or indirectly specific immunity to (i.e., mount an immune response directed against) tumor cells. In preferred embodiments, the immune response results in inhibition of tumor and/or metastatic cell growth and/or proliferation and most preferably results in neoplastic cell death and/or resorption. The immune cells can be derived from a different organism/host (exogenous immune cells) or can be cells obtained from the subject organism (autologous immune cells).

The immune cells are typically activated in vitro by a particular antigen (in this case CAIXv), optionally expanded, and then re-infused back into the source organism (e.g., patient). Methods of performing adoptive immunotherapy are well known to those of skill in the art (see, e.g., U.S. Pat. Nos. 5,081,029, 5,985,270, 5,830,464, 5,776,451, 5,229,115, 690,915, and the like).

In preferred embodiments, this invention contemplates numerous modalities of adoptive immunotherapy, e.g. as described above. In one embodiment, dendritic cells (e.g. isolated from the patient or autologous dendritic cells) are pulsed with CAIXv or the CAIXv-GM-CSF chimeric molecule and then injected back into the subject where they present and activate immune cells in vivo. In addition, or alternatively, the dentritic cells can be transfected with nucleic acids encoding the CAIXv-GM-CSF fusion protein and then re-introduced into a patient.

In another embodiment, modified macrophage or dendritic cell (antigen presenting cells) are pulsed with CAIXv-GM-CSF fusion proteins or transfected with nucleic acids encoding a CAIXv-GM-CSF fusion protein, and then used to stimulate peripheral blood lymphocytes or TIL in culture and activate CAIXv-targeted CTLs that are then infused into the patient.

Similarly, fibroblasts, and other APCs, or tumor cells (e.g. RCCs) are transfected with a nucleic acid expressing a CAIXv-GM-CSF and used to activate tumor cells or PBLs ex vivo to produce CAIXv directed CTLs that can then be infused into a patient.

Similarly various "transfection agents" including, but not limited to gene therapy vectors (e.g. adenovirus, gutless-adenovirus, retrovirus, lentivirus, adeno-associated virus, vaccinia virus etc), cationic lipids, liposomes, dendrimers, and the like, containing or complexed with a nucleic acid encoding a CAIXv-GM-CSF fusion protein are administered to PBLs or to tumor cells (e.g. RCCs) ex vivo to produce CAIXv directed CTLs.

In one particularly preferred embodiments, tumor cells (e.g. RCC cells) transfected to express a CAIXv-GM-CSF protein are used to provide an off-the-shelf vaccine effective against tumors expressing a CAIXv antigen or an antigen that is cross-reactive with CAIXv.

Using the teachings provided herein, other therapeutic modalities utilizing CAIXv-GM-CSF polypeptides or CAIXv-GM-CSF nucleic acids can be readily developed.

As indicated above, in one embodiment the immune cells are derived from peripheral blood lymphocytes or TILs (e.g. derived from tumors/tumor suspension). Lymphocytes used for in vitro activation include, but are not limited to T lymphocytes, various antigen presenting cells (e.g. monocytes, dendritic cells, B cells, etc.) and the like. Activation can involve contacting an antigen presenting cell with the chimeric molecule(s) of this invention which then present the CAIXv antigen (or fragment thereof), e.g., on HLA class I molecules and/or on HLA class II molecules, and/or can involve contacting a cell (e.g. T-lymphocyte) directly with the chimeric molecule. The antigen-presenting cells (APCs), including but not limited to macrophages, dendritic cells and B-cells, are preferably obtained by production in vitro from stem and progenitor cells from human peripheral blood or bone marrow as described by Inaba et al., (1992) J. Exp. Med. 176:1693-1702.

Activation of immune cells can take a number of forms. These include, but are not limited to the direct addition of the chimeric molecule to peripheral blood lymphocytes (PBLs) or tumor infiltrating lymphocytes (TILs) in culture, loading of antigen presenting cells (e.g. monocytes, dendritic cells, etc.) with the chimeric molecule in culture, transfection of antigen presenting cells, or PBLs, with a nucleic acid encoding the GM-CSF-CAIXv chimeric fusion protein, and the like.

APC can be obtained by any of various methods known in the art. In a preferred aspect human macrophages and/or dendritic cells are used, obtained from human blood donors. By way of example but not limitation, PBLs (e.g. T-cells) can be obtained as follows:

Approximately 200 ml of heparinized venous blood is drawn by venipuncture and PBL are isolated by Ficoll-hypaque gradient centrifugation, yielding approximately 1 to $5 \times 10^8$ PBL, depending upon the lymphocyte count of the donor(s). The PBL are washed in phosphate-buffered saline and are suspended at approximately $2 \times 10^5$/ml in RPMI 1640 medium containing 10% pooled heat-inactivated normal human serum; this medium will be referred to as "complete medium."

Similarly, other cells (e.g. mononuclear cells) are isolated from peripheral blood of a patient (preferably the patient to be treated), by Ficoll-Hypaque gradient centrifugation and are seeded on tissue culture dishes which are pre-coated with the patient's own serum or with other AB+ human serum. The cells are incubated at 37° C. for 1 hr, then non-adherent cells are removed by pipetting. To the adherent cells left in the dish, is added cold (4° C.) 1 mM EDTA in phosphate-buffered saline and the dishes are left at room temperature for 15 minutes. The cells are harvested, washed with RPMI buffer and suspended in RPMI buffer. Increased numbers of macrophages may be obtained by incubating at 37° C. with macrophage-colony stimulating factor (M-CSF); increased numbers of dendritic cells may be obtained by incubating with granulocyte-macrophage-colony stimulating factor (GM-CSF) as described in detail by Inaba et al. (1992) J. Exp. Med. 176:1693-1702, and more preferably by incubating with the CAIXv-GM-CSF chimeric molecules of this invention and, optionally IL-4).

The cells (e.g. APCs) are sensitized by contacting/incubating them with the chimeric molecule. In some embodiments, sensitization may be increased by contacting the APCs with heat shock protein(s) (hsp) noncovalently bound to the chimeric molecule. It has been demonstrated that hsps noncovalently bound to antigenic molecules can increase APC sensitization in adoptive immunotherapeutic applications (see, e.g., U.S. Pat. No. 5,885,270).

In one preferred embodiment, e.g. as described in the examples herein, CAIXv-GM-CSF fusion protein (with optional IL-4) is added into the patients PBMC ex vivo and then cultured at 37° C. for 7 days. The culture is re-stimulated weekly with IL-2 and fusion protein, e.g. for 4 to 5 cycles until the culture shows anti-tumor activity against autologous kidney tumor cells displaying CAIXv. The CTLs are then reinfused back into the patient.

For re-infusion, the cells are washed three times and resuspended in a physiological medium preferably sterile, at a convenient concentration (e.g., $1 \times 10^7$/ml) for injection in a patient. The cell suspension is then filtered, e.g., through sterile 110 mesh and put into Fenwall transfer packs. Samples of the cells are tested for the presence of microorganisms including fungi, aerobic and anaerobic bacteria, and mycoplasma. A sample of the cells is optionally retained for immunological testing in order to demonstrate induction of specific immunity.

In a preferred embodiment, before use in immunotherapy, the stimulated lymphocytes are tested for cell-mediated immune reactivity against tumor cells bearing the CAIXv. The PBL/TIL, following stimulation with the chimeric molecules of this invention can be examined with regard to cell surface expression of T and B cell markers by immunofluorescent analysis using fluorescein-conjugated monoclonal antibodies to T and B cell antigens. Expression of known T cell markers, such as the CD4 and CD8 antigens, confirms the identity of the activated lymphocytes as T cells.

The activated cells (e.g. activated T cells) are then, optionally, tested for reactivity against CAIXv. This could be accomplished by any of several techniques known in the art for assaying specific cell-mediated immunity. For example, a cytotoxicity assay, which measures the ability of the stimulated T cells to kill tumor cells bearing the CAIXv or CAIXv antigen in vitro, may be accomplished by incubating the lymphocytes with CAIXv-bearing tumor cells containing a marker (e.g. $^{51}$Cr-labelled cells) and measuring $^{51}$Cr release upon lysis. Such assays have been described (see, e.g., Zarling et al. (1986) J. Immunol. 136: 4669). The activated PBL could also be tested for T helper cell activity by measuring their ability to proliferate, as shown by $^3$H-thymidine incorporation, following stimulation, and/or by measuring their ability to produce lymphokines such as IL-2 or interferon upon stimulation, in the absence of exogenous IL-2. Other assays of specific cell-mediated immunity known in the art, such as leukocyte-adherence inhibition assays (Thomson, D. M. P. (ed.), 1982, Assessment of Immune Status by the Leukocyte Adherence Inhibition Test, Academic Press, New York), may also be used.

Inoculation of the activated cells is preferably through systemic administration. The cells can be administered intravenously through a central venous catheter or into a large peripheral vein. Other methods of administration (for example, direct infusion into an artery) are within the scope of the invention. Approximately $1 \times 10^8$ cells are infused initially and the remainder are infused over the following several hours. In some regimens, patients may optionally receive in addition a suitable dosage of a biological response modifier including but not limited to the cytokines IFN-α, IFN-γ, IL-2, IL-4, IL-6, TNF or other cytokine growth factor, antisense TGFβ, antisense IL-10, and the like. Thus, in some patients, recombinant human IL-2 may be used and will be infused intravenously every 8 hours beginning at the time of T cell infusion. Injections of IL-2 will preferably be at doses of 10,000 to 100,000 units/kg bodyweight, as previously used in cancer patients (Rosenberg et al. (1985) N. Engl. J. Med. 313:1485). The IL-2 infusion maybe continued for several days after infusion of the activated T cells if tolerated by the patient.

Treatment by inoculation of, e.g., activated T cells can be used alone or in conjunction with other therapeutic regimens including but not limited to administration of IL-2 (as described supra), other chemotherapeutics (e.g. doxirubicin, vinblastine, vincristine, etc.), radiotherapy, surgery, and the like.

As indicated above, the cells may, optionally, be expanded in culture. This expansion can be accomplished by repeated stimulation of the T cells with the CAIXv-GM-CSF construct of this invention with or without IL-2 or by growth in medium containing IL-2 alone. Other methods of T cell cultivation (for example with other lymphokines, growth factors, or other bioactive molecules) are also within the scope of the invention. For example, antibodies or their derivative molecules which recognize the Tp67 or Tp44 antigens on T cells have been shown to augment proliferation of activated T cells (Ledbetter et al. (1985) J. Immunol. 135: 2331), and maybe used during in vitro activation to increase proliferation. Interferon has been found to augment the generation of cytotoxic T cells (Zarling et al. (1978) Immunol. 121: 2002), and may be used during in vitro activation to augment the generation of cytotoxic T cells against CAIXv bearing cancer cells.

The description provided above details various methods for isolation, activation, and expansion of PBL. However the present invention provides for the use CAIXv-GM-CSF constructs in various forms, and modifications and adaptations to the method to accommodate these variations. Thus modifications of various adoptive immunotherapeutic approaches utilizing the CAIXv-GM-CSF constructs are within the scope of the invention.

V. Gene Transfer for Systemic Therapy or for Adoptive Immunotherapy

In addition to use of the chimeric GM-CSF-CAIXv chimeric protein for activation in adoptive immunotherapy, cells, (e.g., APCs, PBLs, fibroblasts, TILs, or RCC tumor cells) can be transfected with a vector expressing the chimeric molecule and used for adoptive immunotherapy and/or vaccine therapy.

In one preferred embodiment, the nucleic acid(s) encoding the GM-CSF-CAIXv chimeric fusion proteins are cloned into gene therapy vectors that are competent to transfect cells (such as human or other mammalian cells) in vitro and/or in vivo.

Several approaches for introducing nucleic acids into cells in vivo, ex vivo and in vitro have been used. These include lipid or liposome based gene delivery (WO 96/18372; WO 93/24640; Mannino and Gould-Fogerite (1988) BioTechniques 6(7): 682-691; Rose U.S. Pat. No. 5,279,833; WO 91/06309; and Feigner et al. (1987) Proc. Natl. Acad. Sci. USA 84: 7413-7414) and replication-defective retroviral vectors harboring a therapeutic polynucleotide sequence as part of the retroviral genome (see, e.g., Miller et al. (1990) Mol. Cell. Biol. 10:4239 (1990); Kolberg (1992) J. NIH Res. 4: 43, and Cornetta et al. (1991) Hum. Gene Ther. 2: 215).

For a review of gene therapy procedures, see, e.g., Anderson, Science (1992) 256: 808-813; Nabel and Feigner (1993) TIBTECH 11: 211-217; Mitani and Caskey (1993) TIBTECH 11: 162-166; Mulligan (1993) Science, 926-932; Dillon (1993) TIBTECH 11: 167-175; Miller (1992) Nature 357: 455-460; Van Brunt (1988) Biotechnology 6(10): 1149-1154; Vigne (1995) Restorative Neurology and Neuroscience 8: 35-36; Kremer and Perricaudet (1995) British Medical Bulletin 51(1) 31-44; Haddada et al. (1995) in Current Topics in Microbiology and Immunology, Doerfler and Bohm (eds) Springer-Verlag, Heidelberg Germany; and Yu et al., (1994) Gene Therapy, 1: 13-26.

Widely used retroviral vectors include those based upon murine leukemia virus (MuLV), gibbon ape leukemia virus (GaLV), Simian Immunodeficiency virus (SIV), human immunodeficiency virus (HIV), alphavirus, and combinations thereof (see, e.g., Buchscher et al. (1992) J. Virol. 66(5)2731-2739; Johann et al. (1992) J. Virol. 66 (5):1635-1640 (1992); Sommerfelt et al., (1990) Virol. 176:58-59; Wilson et at (1989) J. Virol. 63:2374-2378; Miller et al., J. Virol. 65:2220-2224 (1991); Wong-Staal et al., PCT/US94/05700, and Rosenburg and Fauci (1993) in Fundamental Immunology, Third Edition Paul (ed) Raven Press, Ltd., New York and the references therein, and Yu et al. (1994) Gene Therapy, supra; U.S. Pat. No. 6,008,535, and the like).

The vectors are optionally pseudotyped to extend the host range of the vector to cells which are not infected by the retrovirus corresponding to the vector. For example, the vesicular stomatitis virus envelope glycoprotein (VSV-G) has been used to construct VSV-G-pseudotyped HIV vectors which can infect hematopoietic stem cells (Naldini et al. (1996) Science 272:263, and Akkina et al. (1996) J. Virol 70:2581).

Adeno-associated virus (AAV)-based vectors are also used to transduce cells with target nucleic acids, e.g., in the in vitro production of nucleic acids and peptides, and in in vivo and ex vivo gene therapy procedures. See, West et al. (1987) Virology 160:38-47; Carter et al. (1989) U.S. Pat. No. 4,797,368; Carter et al. WO 93/24641 (1993); Kotin (1994) Human Gene Therapy 5:793-801; Muzyczka (1994) J. Clin. Invst. 94:1351 for an overview of AAV vectors. Construction of recombinant AAV vectors are described in a number of publications, including Lebkowski, U.S. Pat. No. 5,173,414; Tratschin et al. (1985) Mol. Cell. Biol. 5(11):3251-3260; Tratschin, et al. (1984) Mol. Cell. Biol., 4: 2072-2081; Hermonat and Muzyczka (1984) Proc. Natl. Acad. Sci. USA, 81: 6466-6470; McLaughlin et al. (1988) and Samulski et al. (1989) J. Virol., 63:03822-3828. Cell lines that can be transformed by rAAV include those described in Lebkowski et al. (1988) Mol. Cell. Biol., 8:3988-3996. Other suitable viral vectors include herpes virus, lentivirus, and vaccinia virus.

In addition to viral vectors, a number of non-viral transfection methods are available. Such methods include, but are not limited to electroporation methods, calcium phosphate transfection, liposomes, cationic lipid complexes, water-oil emulsions, polyethylene imines, and dendrimers.

Liposomes were first described in 1965 as a model of cellular membranes and quickly were applied to the delivery of substances to cells. Liposomes entrap DNA by one of two mechanisms which has resulted in their classification as either cationic liposomes or pH-sensitive liposomes. Cationic liposomes are positively charged liposomes which interact with the negatively charged DNA molecules to form a stable complex. Cationic liposomes typically consist of a positively charged lipid and a co-lipid. Commonly used co-lipids include dioleoyl phosphatidylethanolamine (DOPE) or dioleoyl phosphatidylcholine (DOPC). Co-lipids, also called helper lipids, are in most cases required for stabilization of liposome complex. A variety of positively charged lipid formulations are commercially available and many other are under development. Two of the most frequently cited cationic lipids are lipofectamine and lipofectin. Lipofectin is a commercially available cationic lipid first reported by Phil Feigner in 1987 to deliver genes to cells in culture. Lipofectin is a mixture of N-[1-(2,3-dioleyloyx)propyl]-N—N—N-trimethyl ammonia chloride (DOTMA) and DOPE.

DNA and lipofectin or lipofectamine interact spontaneously to form complexes that have a 100% loading efficiency. In other words, essentially all of the DNA is complexed with the lipid, provided enough lipid is available. It is assumed that the negative charge of the DNA molecule interacts with the positively charged groups of the DOTMA. The lipid:DNA ratio and overall lipid concentrations used in forming these complexes are extremely important for efficient gene transfer and vary with application. Lipofectin has been used to deliver linear DNA, plasmid DNA, and RNA to a variety of cells in culture. Shortly after its introduction, it was shown that lipofectin could be used to deliver genes in vivo. Following intravenous administration of lipofectin-DNA complexes, both the lung and liver showed marked affinity for uptake of these complexes and transgene expression. Injection of these complexes into other tissues has had varying results and, for the most part, are much less efficient than lipofectin-mediated gene transfer into either the lung or the liver.

pH-sensitive, or negatively-charged liposomes, entrap DNA rather than complex with it. Since both the DNA and the lipid are similarly charged, repulsion rather than complex formation occurs. Yet, some DNA does manage to get entrapped within the aqueous interior of these liposomes. In some cases, these liposomes are destabilized by low pH and hence the term pH-sensitive. To date, cationic liposomes have been much more efficient at gene delivery both in vivo and in vitro than pH-sensitive liposomes. pH-sensitive liposomes have the potential to be much more efficient at in vivo DNA delivery than their cationic counterparts and should be able to do so with reduced toxicity and interference from serum protein.

In another approach dendrimers complexed to the DNA have been used to transfect cells. Such dendrimers include, but are not limited to, "starburst" dendrimers and various dendrimer polycations.

Dendrimer polycations are three dimensional, highly ordered oligomeric and/or polymeric compounds typically formed on a core molecule or designated initiator by reiterative reaction sequences adding the oligomers and/or polymers and providing an outer surface that is positively changed. These dendrimers may be prepared as disclosed in PCT/US83/02052, and U.S. Pat. Nos. 4,507,466, 4,558,120, 4,568,737, 4,587,329, 4,631,337, 4,694,064, 4,713,975, 4,737,550, 4,871,779, 4,857,599.

Typically, the dendrimer polycations comprise a core molecule upon which polymers are added. The polymers may be oligomers or polymers which comprise terminal groups capable of acquiring a positive charge. Suitable core molecules comprise at least two reactive residues which can be utilized for the binding of the core molecule to the oligomers and/or polymers. Examples of the reactive residues are hydroxyl, ester, amino, imino, imido, halide, carboxyl, carboxyhalide maleimide, dithiopyridyl, and sulfhydryl, among others. Preferred core molecules are ammonia, tris-(2-aminoethyl)amine, lysine, omithine, pentaerythritol and ethylenediamine, among others. Combinations of these residues are also suitable as are other reactive residues.

Oligomers and polymers suitable for the preparation of the dendrimer polycations of the invention are pharmaceutically-acceptable oligomers and/or polymers that are well accepted in the body. Examples of these are polyamidoamines derived from the reaction of an alkyl ester of an .alpha.,.beta.-ethylenically unsaturated carboxylic acid or an .alpha.,.beta.-ethylenically unsaturated amide and an alkylene polyamine or a polyalkylene polyamine, among others. Preferred are methyl acrylate and ethylenediamine. The polymer is preferably covalently bound to the core molecule.

The terminal groups that may be attached to the oligomers and/or polymers should be capable of acquiring a positive charge. Examples of these are azoles and primary, secondary, tertiary and quaternary aliphatic and aromatic amines and azoles, which may be substituted with S or O, guanidinium, and combinations thereof. The terminal cationic groups are preferably attached in a covalent manner to the oligomers and/or polymers. Preferred terminal cationic groups are amines and guanidinium. However, others may also be utilized. The terminal cationic groups may be present in a proportion of about 10 to 100% of all terminal groups of the oligomer and/or polymer, and more preferably about 50 to 100%.

The dendrimer polycation may also comprise 0 to about 90% terminal reactive residues other than the cationic groups. Suitable terminal reactive residues other than the terminal cationic groups are hydroxyl, cyano, carboxyl, sulfhydryl, amide and thioether, among others, and combinations thereof. However others may also be utilized.

The dendrimer polycation is generally and preferably non-covalently associated with the polynucleotide. This permits an easy disassociation or disassembling of the composition once it is delivered into the cell. Typical dendrimer polycation suitable for use herein have a molecular weight ranging from about 2,000 to 1,000,000 Da, and more preferably about 5,000 to 500,000 Da. However, other molecule weights are also suitable. Preferred dendrimer polycations have a hydrodynamic radius of about 11 to 60.ANG., and more preferably about 15 to 55.ANG. Other sizes, however, are also suitable. Methods for the preparation and use of dendrimers in gene therapy are well known to those of skill in the art and describe in detail, for example, in U.S. Pat. No. 5,661,025.

Where appropriate, two or more types of vectors can be used together. For example, a plasmid vector may be used in conjunction with liposomes. In the case of non-viral vectors, nucleic acid may be incorporated into the non-viral vectors by any suitable means known in the art. For plasmids, this typically involves ligating the construct into a suitable restriction site. For vectors such as liposomes, water-oil emulsions, polyethylene amines and dendrimers, the vector and construct may be associated by mixing under suitable conditions known in the art.

VI. Administration of GM-CSF-CAIXv with Other Agents

In various embodiments, the GM-CSF-CAIXv fusion proteins, or nucleic acids encoding the GM-CSF-CAIXv fusion proteins can be administered in conjunction with other agents. Such agents include, but are not limited to various chemotherapeutic agents (e.g. doxirubicin and derivatives, taxol and derivatives, vinblastine, vincristine, camptothecin derivatives, and the like, various cytokines (e.g. IL-2, IL-7, IL-12, IFN, etc.), various cytotoxins (e.g. *Pseudomonas* exotoxin and derivatives, diphtheria toxin and derivatives, ricin and derivatives, abrin and derivatives, thymidine kinase and derivatives), antisense molecules (e.g. antisense IL-10, TGF-β., etc.), antibodies against various growth factors/receptors (e.g. anti-VEGF, anti-EGFR, anti-IL-8, anti-FGF etc.), and the like. The methods of this invention can also be used as a adjunct to surgery, and/or radiotherapy.

VII. Kits

Kits of the invention are provided that include materials/reagents useful for vaccination using a polypeptide antigen (GM-CSF-CAIXv polypeptide) and/or DNA vaccination, and/or adoptive immunotherapy. Kits optimized for GM-CSF-CAIXv polypeptide vaccination preferably comprise a container containing a GM-CSF-CAIXv chimeric molecule. The molecule can be provided in solution, in suspension, or as a (e.g. lyophilized) powder. The GM-CSF-CAIXv may be packaged with appropriate pharmaceutically acceptable excipient and/or adjuvant, e.g. in a unit dosage form.

Similarly, kits optimized for DNA vaccination of a construct encoding a GM-CSF-CAIXv polypeptide preferably comprise a container containing a GM-CSF-CAIXv nucleic acid (e.g. a DNA). As with the polypeptide, the nucleic acid can be provided in solution, in suspension, or as a (e.g. lyophilized) powder. The GM-CSF-CAIXv nucleic may be packaged with appropriate pharmaceutically acceptable excipient and/or facilitating agent(s), e.g. in a unit dosage form. The kit can further include reagents and/or devices to facilitate delivery of the nucleic acid to the subject (e.g. human or non-human mammal).

Kits optimized for adoptive immunotherapy typically include a container containing a chimeric GM-CSF-CAIXv polypeptide as described above. The kits may optionally include a nucleic acid (e.g. a vector) encoding a GM-CSF-CAIXv fusion protein for ex vivo transfection of cells. Such kits may also, optionally, include various cell lines (e.g. RCC) and/or reagents (e.g. IL-2) to facilitate expansion of activated cells.

The kits can, optionally, include additional reagents (e.g. buffers, drugs, cytokines, cells/cell lines, cell culture media, etc.) and/or devices (e.g. syringes, biolistic devices, etc.) for the practice of the methods of this invention.

In addition, the kits may include instructional materials containing directions (i.e., protocols) for the practice of the methods of this invention. Thus typical instructional materials will teach the use of GM-CSF-CAIXv chimeric molecules (or the nucleic acid encoding such) as vaccines, DNA vaccines, or adoptive immunotherapeutic agents in the treatment of renal cell cancers. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

Additional Features

The novel CAIX variant provided herein can also be used for additional research, diagnostic and therapeutic purposes. Specific blockers of CAIXv and/or high-affinity agonists for CAIXv can be exploited as novel therapeutic agents. In addition, even more potent and specific GMCSF-CAIXv based therapies (for example, therapies targeting RCC) can be achieved using a nanotechnology platform.

The novel CAIXv cDNA/amino acidic sequences unreported previously provide a novel mechanism and signaling pathway for RCC with significant prognostic and therapeutic capabilities, as well as the promising potential with regard to develop new pharmacological agents and strategies to target RCC and other CAIXv-expressing cancers.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety, to the extent not inconsistent with the present disclosure, for all purposes to the same extent as if each individual publication, patent, patent application, and/or other document were individually indicated to be incorporated by reference for all purposes.

What is claimed is:

1. A method of inhibiting the proliferation or growth of a transformed cell that bears a carbonic anhydrase IX (CAIX) variant, wherein the transformed cell is a renal cancer cell, cervical cancer cell, bladder cancer cell, or hypoxia-inducible cancer cell, said method comprising:
 obtaining an immune cell selected from the group consisting of a dendritic cell, an antigen presenting cell, a B lymphocyte, a T cell, a peripheral blood lymphocyte, and a tumor infiltrating lymphocyte;
 activating said immune cell by (i) contacting the immune cell with a CAIX variant protein comprising SEQ ID NO: 1 or a fragment thereof comprising the amino acids G121 and S374, wherein the CAIX variant protein is attached to a granulocyte macrophage colony stimulating factor (GM-CSF) or a fragment thereof, or (ii) transfecting the immune cell with a construct comprising a nucleic acid encoding a chimeric fusion protein comprising GM-CSF attached to the CAIX variant protein, wherein the CAIX variant protein comprises SEQ ID NO:1 or a fragment thereof comprising the amino acids G121 and S374; and
 infusing the activated cell into a mammal containing the transformed cell bearing the CAIX variant.

2. The method of claim 1, wherein the immune cell is a peripheral blood lymphocyte or a tumor infiltrating lymphocyte.

3. The method of claim 1, wherein the infusing step comprises infusing the activated cells into the mammal from which the immune cell was obtained.

4. The method of claim 1, wherein said immune cell is a dendritic cell.

5. The method of claim 1, wherein the activating step comprises contacting the immune cell with the CAIX variant protein attached to GM-CSF.

6. The method of claim 1, wherein the activating step comprises transfecting the immune cell with the construct comprising the nucleic acid encoding the chimeric fusion protein.

7. The method of claim 1, wherein the CAIX variant protein comprises SEQ ID NO:1.

8. The method of claim 1, wherein the GM-CSF is a human GM-CSF.

9. The method of claim 1, wherein the CAIX variant and the GM-CSF are joined by a peptide linker ranging in length from 2 to about 20 amino acids.

10. The method of claim 9, wherein the peptide linker comprises -Arg-Arg or -Lys-Leu-.

11. The method of claim 1, wherein subsequent to the activating step, the method further comprises expanding the activated cell in culture.

12. The method of claim 11, wherein the expanding step comprises contacting the activated cell with a cytokine.

13. The method of claim 12, wherein the cytokine is IL-2, interferon α, or interferon γ.

14. The method of claim 1, wherein the transformed cell is a renal cancer cell.

15. The method of claim 14, wherein the transformed renal cancer cell is a renal cell carcinoma cell.

16. The method of claim 1, wherein the mammal is a human.

* * * * *

SEQUENCE LISTING

```
<160> NUMBER OF SEQ ID NOS: 8

<210> SEQ ID NO 1
<211> LENGTH: 459
<212> TYPE: PRT
<213> ORGANISM: Homo sapiens
<220> FEATURE:
<221> NAME/KEY: VARIANT
<222> LOCATION: (1)..(459)
<223> OTHER INFORMATION: human carbonic anhydrase IX (CAIX) variant
      (CAIXv)

<400> SEQUENCE: 1

Met Ala Pro Leu Cys Pro Ser Pro Trp Leu Pro Leu Leu Ile Pro Ala
1               5                   10                  15

Pro Ala Pro Gly Leu Thr Val Gln Leu Leu Leu Ser Leu Leu Leu Leu
            20                  25                  30

Met Pro Val His Pro Gln Arg Leu Pro Arg Met Gln Glu Asp Ser Pro
```

```
                35                  40                  45
Leu Gly Gly Ser Ser Gly Glu Asp Asp Pro Leu Gly Glu Glu Asp
             50                  55                  60

Leu Pro Ser Glu Glu Asp Ser Pro Arg Glu Glu Asp Pro Gly Glu
 65                  70                  75                  80

Glu Asp Leu Pro Gly Glu Asp Leu Pro Gly Glu Glu Asp Leu Pro
                 85                  90                  95

Glu Val Lys Pro Lys Ser Glu Glu Gly Ser Leu Lys Leu Glu Asp
                100                 105                 110

Leu Pro Thr Val Glu Ala Pro Gly Gly Pro Gln Glu Pro Gln Asn Asn
             115                 120                 125

Ala His Arg Asp Lys Glu Gly Asp Asp Gln Ser His Trp Arg Tyr Gly
             130                 135                 140

Gly Asp Pro Pro Trp Pro Arg Val Ser Pro Ala Cys Ala Gly Arg Phe
145                 150                 155                 160

Gln Ser Pro Val Asp Ile Arg Pro Gln Leu Ala Ala Phe Cys Pro Ala
                165                 170                 175

Leu Arg Pro Leu Glu Leu Leu Gly Phe Gln Leu Pro Pro Leu Pro Glu
             180                 185                 190

Leu Arg Leu Arg Asn Asn Gly His Ser Val Gln Leu Thr Leu Pro Pro
             195                 200                 205

Gly Leu Glu Met Ala Leu Gly Pro Gly Arg Glu Tyr Arg Ala Leu Gln
210                 215                 220

Leu His Leu His Trp Gly Ala Ala Gly Arg Pro Gly Ser Glu His Thr
225                 230                 235                 240

Val Glu Gly His Arg Phe Pro Ala Glu Ile His Val Val His Leu Ser
                245                 250                 255

Thr Ala Phe Ala Arg Val Asp Glu Ala Leu Gly Arg Pro Gly Gly Leu
             260                 265                 270

Ala Val Leu Ala Ala Phe Leu Glu Glu Gly Pro Glu Glu Asn Ser Ala
             275                 280                 285

Tyr Glu Gln Leu Leu Ser Arg Leu Glu Glu Ile Ala Glu Glu Gly Ser
    290                 295                 300

Glu Thr Gln Val Pro Gly Leu Asp Ile Ser Ala Leu Leu Pro Ser Asp
305                 310                 315                 320

Phe Ser Arg Tyr Phe Gln Tyr Glu Gly Ser Leu Thr Thr Pro Pro Cys
                325                 330                 335

Ala Gln Gly Val Ile Trp Thr Val Phe Asn Gln Thr Val Met Leu Ser
             340                 345                 350

Ala Lys Gln Leu His Thr Leu Ser Asp Thr Leu Trp Gly Pro Gly Asp
             355                 360                 365

Ser Arg Leu Gln Leu Ser Phe Arg Ala Thr Gln Pro Leu Asn Gly Arg
    370                 375                 380

Val Ile Glu Ala Ser Phe Pro Ala Gly Val Asp Ser Ser Pro Arg Ala
385                 390                 395                 400

Ala Glu Pro Val Gln Leu Asn Ser Cys Leu Ala Ala Gly Asp Ile Leu
                405                 410                 415

Ala Leu Val Phe Gly Leu Leu Phe Ala Val Thr Ser Val Ala Phe Leu
             420                 425                 430

Val Gln Met Arg Arg Gln His Arg Arg Gly Thr Lys Gly Gly Val Ser
             435                 440                 445

Tyr Arg Pro Ala Glu Val Ala Glu Thr Gly Ala
    450                 455
```

<210> SEQ ID NO 2
<211> LENGTH: 1380
<212> TYPE: DNA
<213> ORGANISM: Homo sapiens
<220> FEATURE:
<221> NAME/KEY: misc_feature
<222> LOCATION: (1)..(1380)
<223> OTHER INFORMATION: human carbonic anhydrase IX (CAIX) variant
      (CAIXv)

<400> SEQUENCE: 2

```
atggctcccc tgtgcccag ccctggctc cctctgttga tcccggcccc tgctccaggc      60
ctcactgtgc aactgctgct gtcactgctg cttctgatgc ctgtccatcc ccagaggttg    120
ccccggatgc aggaggattc ccccttggga ggaggctctt ctggggaaga tgacccactg    180
ggcgaggagg atctgcccag tgaagaggat tcgcccagag aggaggatcc acccggagag    240
gaggatctac ctggagagga ggatctacct ggagaggagg atctacctga agttaagcct    300
aaatcagaag aagagggctc cctgaagtta gaggatctac ctaccgttga ggctcctgga    360
ggtcctcaag aaccccagaa taatgcccac aggacaaag aaggggatga ccagagtcat    420
tggcgctatg gagcgacccc gccctggccc cgggtgtccc cagcctgcgc gggccgcttc    480
cagtccccgg tggatatccg ccccagctc gccgccttct gccggccct cgccccctg      540
gaactcctgg gcttccagct cccgccgctc ccagaactgc gcctgcgcaa caatggccac    600
agtgtgcaac tgaccctgcc tcctgggcta gagatggctc tgggtcccgg gcgggagtac    660
cgggctctgc agctgcatct gcactggggg gctgcaggtc gtccgggctc ggagcacact    720
gtggaaggcc accgtttccc tgccgagatc acgtggttc acctcagcac cgcctttgcc    780
agagttgacg aggccttggg gcgccccggga ggcctggccg tgttggccgc ctttctggag    840
gagggcccgg aagaaacag tgcctatgag cagttgctgt ctcgcttgga gaaatcgct    900
gaggaaggct cagagactca ggtcccagga ctggacatat ctgcactcct gccctctgac    960
ttcagccgct acttccaata tgaggggtct ctgactacac cgcctgtgc ccagggtgtc   1020
atctggactg tgtttaacca gacagtaatg ctgagtgcta agcagctcca caccctctct   1080
gacaccctgt ggggacccgg tgactctcgg ctacaactga gcttccgagc gacgcagcct   1140
ttgaatgggc gagtgattga ggcctccttc cctgctggag tggacagcag tcctcgggct   1200
gctgagccag tccagctgaa ttcctgcctg gctgctggtg acattctagc cctggttttt   1260
ggcctccttt ttgctgtcac cagcgtcgcg ttccttgtgc agatgagaag gcagcacaga   1320
aggggaacca aggggggtgt gagctaccgc ccagcagagg tagccgagac tggagcctag   1380
```

<210> SEQ ID NO 3
<211> LENGTH: 459
<212> TYPE: PRT
<213> ORGANISM: Homo sapiens
<220> FEATURE:
<221> NAME/KEY: VARIANT
<222> LOCATION: (1)..(459)
<223> OTHER INFORMATION: human carbonic anhydrase IX (CAIX, CA9), renal
      cell carcinoma associated antigen G250, MN

<400> SEQUENCE: 3

Met Ala Pro Leu Cys Pro Ser Pro Trp Leu Pro Leu Leu Ile Pro Ala
1               5                   10                  15

Pro Ala Pro Gly Leu Thr Val Gln Leu Leu Leu Ser Leu Leu Leu Leu
                20                  25                  30

-continued

```
Met Pro Val His Pro Gln Arg Leu Pro Arg Met Gln Glu Asp Ser Pro
             35                  40                  45
Leu Gly Gly Gly Ser Ser Gly Glu Asp Asp Pro Leu Gly Glu Glu Asp
 50                  55                  60
Leu Pro Ser Glu Glu Asp Ser Pro Arg Glu Glu Asp Pro Pro Gly Glu
 65                  70                  75                  80
Glu Asp Leu Pro Gly Glu Glu Asp Leu Pro Gly Glu Glu Asp Leu Pro
                 85                  90                  95
Glu Val Lys Pro Lys Ser Glu Glu Gly Ser Leu Lys Leu Glu Asp
                100                 105                 110
Leu Pro Thr Val Glu Ala Pro Gly Asp Pro Gln Glu Pro Gln Asn Asn
            115                 120                 125
Ala His Arg Asp Lys Glu Gly Asp Gln Ser His Trp Arg Tyr Gly
        130                 135                 140
Gly Asp Pro Pro Trp Pro Arg Val Ser Pro Ala Cys Ala Gly Arg Phe
145                 150                 155                 160
Gln Ser Pro Val Asp Ile Arg Pro Gln Leu Ala Ala Phe Cys Pro Ala
                165                 170                 175
Leu Arg Pro Leu Glu Leu Leu Gly Phe Gln Leu Pro Pro Leu Pro Glu
            180                 185                 190
Leu Arg Leu Arg Asn Asn Gly His Ser Val Gln Leu Thr Leu Pro Pro
        195                 200                 205
Gly Leu Glu Met Ala Leu Gly Pro Gly Arg Glu Tyr Arg Ala Leu Gln
            210                 215                 220
Leu His Leu His Trp Gly Ala Ala Gly Arg Pro Gly Ser Glu His Thr
225                 230                 235                 240
Val Glu Gly His Arg Phe Pro Ala Glu Ile His Val Val His Leu Ser
                245                 250                 255
Thr Ala Phe Ala Arg Val Asp Glu Ala Leu Gly Arg Pro Gly Gly Leu
            260                 265                 270
Ala Val Leu Ala Ala Phe Leu Glu Glu Gly Pro Glu Glu Asn Ser Ala
        275                 280                 285
Tyr Glu Gln Leu Leu Ser Arg Leu Glu Glu Ile Ala Glu Glu Gly Ser
290                 295                 300
Glu Thr Gln Val Pro Gly Leu Asp Ile Ser Ala Leu Leu Pro Ser Asp
305                 310                 315                 320
Phe Ser Arg Tyr Phe Gln Tyr Glu Gly Ser Leu Thr Thr Pro Pro Cys
                325                 330                 335
Ala Gln Gly Val Ile Trp Thr Val Phe Asn Gln Thr Val Met Leu Ser
            340                 345                 350
Ala Lys Gln Leu His Thr Leu Ser Asp Thr Leu Trp Gly Pro Gly Asp
        355                 360                 365
Ser Arg Leu Gln Leu Asn Phe Arg Ala Thr Gln Pro Leu Asn Gly Arg
    370                 375                 380
Val Ile Glu Ala Ser Phe Pro Ala Gly Val Asp Ser Ser Pro Arg Ala
385                 390                 395                 400
Ala Glu Pro Val Gln Leu Asn Ser Cys Leu Ala Ala Gly Asp Ile Leu
                405                 410                 415
Ala Leu Val Phe Gly Leu Leu Phe Ala Val Thr Ser Val Ala Phe Leu
            420                 425                 430
Val Gln Met Arg Arg Gln His Arg Arg Gly Thr Lys Gly Gly Val Ser
        435                 440                 445
Tyr Arg Pro Ala Glu Val Ala Glu Thr Gly Ala
```

<210> SEQ ID NO 4
<211> LENGTH: 144
<212> TYPE: PRT
<213> ORGANISM: Homo sapiens
<220> FEATURE:
<221> NAME/KEY: VARIANT
<222> LOCATION: (1)..(144)
<223> OTHER INFORMATION: human granulocyte-macrophage colony stimulating
      factor (GM-CSF, GMCSF, hGMCSF), colony stimulating factor 2
      (granulocyte-macrophage) (CSF2)

<400> SEQUENCE: 4

Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile Ser Glu Met Phe
    50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Thr Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence:flexible
      extended conformation peptide linker (spacer)

<400> SEQUENCE: 5

Gly Gly Gly Gly Ser Gly Gly Gly Gly Ser
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence:flexible
      extended conformation peptide linker (spacer)

<400> SEQUENCE: 6

Ala Gly Ser Ala Gly Ser Ala Gly Ser Ala Gly Ser
1               5                   10

<210> SEQ ID NO 7
<211> LENGTH: 1818
<212> TYPE: DNA
<213> ORGANISM: Artificial Sequence
<220> FEATURE:
<223> OTHER INFORMATION: Description of Artificial Sequence:chimeric
      fusion protein (hGMCSF)-(linker)-(CAIXv), GMCSF-CAIXv

<400> SEQUENCE: 7

```
atgtggctgc agagcctgct gctcttgggc actgtggcct gcagcatctc tgcacccgcc      60
cgctcgccca gccccagcac gcagccctgg gagcatgtga atgccatcca ggaggcccgg     120
cgtctcctga acctgagtag agacactgct gctgagatga tgaaacagt agaagtcatc     180
tcagaaatgt ttgacctcca ggagccgacc tgcctacaga cccgcctgga gctgtacaag     240
cagggcctgc ggggcagcct caccaagctc aagggcccct tgaccatgat ggccagccac     300
tacaagcagc actgccctcc aaccccggaa acttcctgtg caacccagac tatcaccttt     360
gaaagtttca agagaacct gaaggacttt ctgcttgtca tcccctttga ctgctgggag     420
ccagtccagg agaagcttat ggctcccctg tgccccagcc cctggctccc tctgttgatc     480
ccggcccctg ctccaggcct cactgtgcaa ctgctgctgt cactgctgct tctgatgcct     540
gtccatcccc agaggttgcc ccggatgcag gaggattccc ccttgggagg aggctcttct     600
ggggaagatg acccactggg cgaggaggat ctgcccagtg aagaggattc gcccagagag     660
gaggatccac ccggagagga ggatctacct ggagaggagg atctacctgg agaggaggat     720
ctacctgaag ttaagcctaa atcagaagaa gagggctccc tgaagttaga ggatctacct     780
accgttgagg ctcctggagg tcctcaagaa ccccagaata atgcccacag ggacaaagaa     840
ggggatgacc agagtcattg cgctatggga ggcgaccccg cctggccccg ggtgtcccca     900
gcctgcgcgg gccgcttcca gtccccggtg gatatccgcc ccagctcgc cgccttctgc     960
ccggccctgc gccccctgga actcctgggc ttccagctcc cgccgctccc agaactgcgc    1020
ctgcgcaaca atggccacag tgtgcaactg accctgcctc ctgggctaga gatggctctg    1080
ggtcccgggc gggagtaccg ggctctgcag ctgcatctgc actgggggc tgcaggtcgt    1140
ccgggctcgg agcacactgt ggaaggccac cgtttccctg ccgagatcca cgtggttcac    1200
ctcagcaccg cctttgccag agttgacgag gccttgggc gccgggagg cctggccgtg    1260
ttggccgcct ttctggagga gggcccggaa gaaaacagtg cctatgagca gttgctgtct    1320
cgcttggaag aaatcgctga ggaaggctca gagactcagg tcccaggact ggacatatct    1380
gcactcctgc cctctgactt cagccgctac ttccaatatg aggggtctct gactacaccg    1440
ccctgtgccc agggtgtcat ctggactgtg tttaaccaga cagtaatgct gagtgctaag    1500
cagctccaca ccctctctga caccctgtgg ggacccggtg actctcggct acaactgagc    1560
ttccgagcga cgcagccttt gaatgggcga gtgattgagg cctccttccc tgctggagtg    1620
gacagcagtc tcgggctgc tgagccagtc cagctgaatt cctgcctggc tgctggtgac    1680
attctagccc tggttttttgg cctcctttttt gctgtcacca gcgtcgcgtt ccttgtgcag    1740
atgagaaggc agcacagaag gggaaccaaa gggggtgtga gctaccgccc agcagaggta    1800
gccgagactg gagcctag                                                  1818
```

<210> SEQ ID NO 8
<211> LENGTH: 605
<212> TYPE: PRT
<213> ORGANISM: Artificial Sequence
<220> FEATURE:
<223> OTHER INFORMATION: Description of Artificial Sequence:chimeric
      fusion protein (hGMCSF)-(linker)-(CAIXv), GMCSF-CAIXv

<400> SEQUENCE: 8

Met Trp Leu Gln Ser Leu Leu Leu Leu Gly Thr Val Ala Cys Ser Ile
1               5                   10                  15

-continued

Ser Ala Pro Ala Arg Ser Pro Ser Pro Ser Thr Gln Pro Trp Glu His
         20                  25                  30

Val Asn Ala Ile Gln Glu Ala Arg Arg Leu Leu Asn Leu Ser Arg Asp
         35                  40                  45

Thr Ala Ala Glu Met Asn Glu Thr Val Glu Val Ile Ser Glu Met Phe
65       50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                 85                  90                  95

Met Ala Ser His Tyr Lys Gln His Cys Pro Pro Thr Pro Glu Thr Ser
                 100                 105                 110

Cys Ala Thr Gln Thr Ile Thr Phe Glu Ser Phe Lys Glu Asn Leu Lys
                 115                 120                 125

Asp Phe Leu Leu Val Ile Pro Phe Asp Cys Trp Glu Pro Val Gln Glu
130                 135                 140

Lys Leu Met Ala Pro Leu Cys Pro Ser Pro Trp Leu Pro Leu Leu Ile
145                 150                 155                 160

Pro Ala Pro Ala Pro Gly Leu Thr Val Gln Leu Leu Ser Leu Leu
                 165                 170                 175

Leu Leu Met Pro Val His Pro Gln Arg Leu Pro Arg Met Gln Glu Asp
                 180                 185                 190

Ser Pro Leu Gly Gly Gly Ser Ser Gly Glu Asp Asp Pro Leu Gly Glu
                 195                 200                 205

Glu Asp Leu Pro Ser Glu Glu Asp Ser Pro Arg Glu Glu Asp Pro Pro
210                 215                 220

Gly Glu Glu Asp Leu Pro Gly Glu Glu Asp Leu Pro Gly Glu Glu Asp
225                 230                 235                 240

Leu Pro Glu Val Lys Pro Lys Ser Glu Glu Gly Ser Leu Lys Leu
                 245                 250                 255

Glu Asp Leu Pro Thr Val Glu Ala Pro Gly Gly Pro Gln Glu Pro Gln
                 260                 265                 270

Asn Asn Ala His Arg Asp Lys Glu Gly Asp Asp Gln Ser His Trp Arg
                 275                 280                 285

Tyr Gly Gly Asp Pro Pro Trp Pro Arg Val Ser Pro Ala Cys Ala Gly
                 290                 295                 300

Arg Phe Gln Ser Pro Val Asp Ile Arg Pro Gln Leu Ala Ala Phe Cys
305                 310                 315                 320

Pro Ala Leu Arg Pro Leu Glu Leu Leu Gly Phe Gln Leu Pro Pro Leu
                 325                 330                 335

Pro Glu Leu Arg Leu Arg Asn Asn Gly His Ser Val Gln Leu Thr Leu
                 340                 345                 350

Pro Pro Gly Leu Glu Met Ala Leu Gly Pro Gly Arg Glu Tyr Arg Ala
                 355                 360                 365

Leu Gln Leu His Leu His Trp Gly Ala Ala Gly Arg Pro Gly Ser Glu
                 370                 375                 380

His Thr Val Glu Gly His Arg Phe Pro Ala Glu Ile His Val Val His
385                 390                 395                 400

Leu Ser Thr Ala Phe Ala Arg Val Asp Glu Ala Leu Gly Arg Pro Gly
                 405                 410                 415

Gly Leu Ala Val Leu Ala Ala Phe Leu Glu Glu Gly Pro Glu Glu Asn
                 420                 425                 430

Ser Ala Tyr Glu Gln Leu Leu Ser Arg Leu Glu Glu Ile Ala Glu Glu

```
                    435                 440                 445
Gly Ser Glu Thr Gln Val Pro Gly Leu Asp Ile Ser Ala Leu Leu Pro
        450                 455                 460

Ser Asp Phe Ser Arg Tyr Phe Gln Tyr Glu Gly Ser Leu Thr Thr Pro
465                 470                 475                 480

Pro Cys Ala Gln Gly Val Ile Trp Thr Val Phe Asn Gln Thr Val Met
            485                 490                 495

Leu Ser Ala Lys Gln Leu His Thr Leu Ser Asp Thr Leu Trp Gly Pro
                500                 505                 510

Gly Asp Ser Arg Leu Gln Leu Ser Phe Arg Ala Thr Gln Pro Leu Asn
            515                 520                 525

Gly Arg Val Ile Glu Ala Ser Phe Pro Ala Gly Val Asp Ser Ser Pro
    530                 535                 540

Arg Ala Ala Glu Pro Val Gln Leu Asn Ser Cys Leu Ala Ala Gly Asp
545                 550                 555                 560

Ile Leu Ala Leu Val Phe Gly Leu Leu Phe Ala Val Thr Ser Val Ala
            565                 570                 575

Phe Leu Val Gln Met Arg Arg Gln His Arg Arg Gly Thr Lys Gly Gly
                580                 585                 590

Val Ser Tyr Arg Pro Ala Glu Val Ala Glu Thr Gly Ala
        595                 600                 605
```